(12) United States Patent
Nolan et al.

(10) Patent No.: US 7,332,356 B2
(45) Date of Patent: *Feb. 19, 2008

(54) FLUORESCENT DYE BINDING PEPTIDES

(75) Inventors: Garry P. Nolan, Palo Alto, CA (US); Michael N. Rozinov, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 627 days.

This patent is subject to a terminal disclaimer.

(21) Appl. No.: 10/692,151

(22) Filed: Oct. 14, 2003

(65) Prior Publication Data

US 2004/0176578 A1    Sep. 9, 2004

Related U.S. Application Data

(63) Continuation of application No. 09/419,381, filed on Oct. 15, 1999, now Pat. No. 6,747,135.

(60) Provisional application No. 60/104,465, filed on Oct. 16, 1998.

(51) Int. Cl.
   *G01N 33/533*   (2006.01)
   *G01N 33/532*   (2006.01)
   *A61K 38/10*    (2006.01)

(52) U.S. Cl. .................. 436/546; 435/544; 435/86; 530/327

(58) Field of Classification Search ............ 436/544, 436/546, 86; 530/327, 328, 401
   See application file for complete search history.

(56) References Cited

U.S. PATENT DOCUMENTS

5,491,074 A    2/1996   Aldwin et al.
6,747,135 B1   6/2004   Nolan et al.

OTHER PUBLICATIONS

Adey et. al. "Identification of Calmodulin-Binding Peptide Consensus Sequences from a Phage-Displayed Random Peptide Library," *Gene.* 169(1):133-4, (1996).

Apletalina et. al. "Identification of Inhibitors of Prohormone Convertases 1 and 2 Using a Peptide Combinatorial Library," *J. Biol. Chem.* 273(41): 133-4, (1998).

Caparon, M.H., De Ciechi, P.A., Devine, C.S., Olins, P.O. & Lee, S.C. "Analysis of novel streptavidin-binding peptides, identified using a phage display library, shows that amino acids external to a perfectly conserved consensus sequence and to the presented peptides contribute to binding" *Mol Divers* 1, 241-246 (1996).

Chen, C.T., Wagner, H. & Still, W.C. "Fluorescent, sequence-selective peptide detection by synthetic small molecules," *Science* 279, 851-853, (1998).

(Continued)

*Primary Examiner*—Long V. Le
*Assistant Examiner*—Shafiqul Haq
(74) *Attorney, Agent, or Firm*—Bozicevic, Field & Francis LLP; Carol L. Francis

(57) ABSTRACT

The present invention is directed to novel polypeptides, termed fluorettes, that bind with high avidity to fluorophore dyes. The peptides find use in a variety of methods and approaches involving fluorophore dyes.

15 Claims, 8 Drawing Sheets

Fluorescein carrier

Rhodamine Red carrier

Oregon Green 514 carrier

Texas Red carrier

OTHER PUBLICATIONS

Cheng et. al. "Selection of Peptides that Functionally Replace a Zinc Finger in the Sp1 Transcription Factor by Using a Yeast Combinatorial Library," *Proc. Natl. Acad. Sci. USA.* 94(25):14120-5, (Dec. 1997).

Cull, M.G., Miller, J.F. &Schatz, P.J. "Screening for receptor ligands using large libraries of peptides linked to the C terminus of the lac repressor," *Proc. Natl. Acad. Sci.* USA 89(5): 1865-1869, (Mar. 1992).

Cwirla, S.E., Peters, E.A., Barrett, R.W. & Dower, W.J. "Peptides on phage: a vas library of peptides for identifying ligands," *Proc. Natl. Acad. Sci.* USA 87, 6378-6382, (Aug. 1990).

DeGraaf et. al. "Biochemical Diversity in a Phage Display Library of Random Decapeptides," *Gene.* 128(1): 13-7, (1993).

Devlin, J.J., Panganiban, L.C. & Devlin, P.E. "Random peptide libraries: a source of specific protein binding molecules," *Science* 249, 404-406, (1990).

Dybwad et. al. "Identification of New B Cell Epitopes in the Sera of Rheumatoid Arthritis Patients Using a Random Nanopeptide Phage Library," *Eur. J. Immunol.* 23(12): 3189-93, (1993).

Griffin, B.A., Adams, S.R. & Tsien, R.Y., "Specific covalent labeling of recombinant protein molecules inside live cells," *Science* 281, 269-272, (1998).

Hanes, J. & Pluckthun, A. "In vitro selection and evolution of functional proteins by using ribosome display," *Proc. Natl. Acad. Sci. U.S.A.* 94, 4937-4942, (1997).

Harrison, J.L., Williams, S.C., Winter, G. & Nissim, "A Screening of phage antibody libraries," *Methods Enzymol.* 267, 83-109, (1996).

Jayawickreme et.al. "Creation and Functional Screening of a Multi-Use Peptide Library," *Proc. Natl. Acad. Sci.* USA. 91(5): 1614-8, (1994).

Katz, B.A. "Binding to protein targets of peptidic leads discovered by phage display: crystal structures of streptavidin-bound linear and cyclic peptide ligands containing the HPQ sequence," *Biochemistry* 34, 15421-15429, (1995).

Koivunen, E., Wang, B. & Ruoslahti, E. "Phage libraries displaying cyclic peptides with different ring sizes: ligand specificities of the RGD-directed integrins," *Biotechnology* 13, 265-270, (1995).

Krasnow et al. "Whole animal cell sorting of drosphila embryos", *Science.* vol. 251, 81-85 (1991).

Lam et. al. "Application of 'One Bed One-Compound' Combinatorial Library Methods in Signal Transduction Research," *Life Sci.* 62(17-18): 1577-83, (1998).

Lam, KS. "Application of Combinatorial Library Methods in Cancer Research and Drug Discovery," *Anticancer Drug Des.* 12(3): 145-67, (1997).

Lefevre, et. al. "Texas Red-X and Rhodamine Red-X, New Derivatives of Sulforhodamine 101 and Lissamine Rhodamine B with Improved Labeling and Fluorescence Properties," *Bioconjugate Chem.*, 7, 482-489 (1996).

Lorincz et al., "Enzyme-generated intracellular fluorescence for single-cell reporter gene analysis utilizing *escherichia coli* β-glucuronidas", *Cytometry* 24:321-329 (1996).

Mattheakis, L.C., Bhatt, R.R. & Dower, W.J., "An in vitro polysome display system for identifying ligand from very large peptide libraries," *Proc, Natl. Acad. Sci. U.S.A.* 91, 9022-9026, (1994).

Matthews, D.J. & Wells, J.A. "Substrate phage: selection of protease substrates by monovalent phage display," *Science* 260, 1113-1117, (1993).

Misteli and Spector, "Applications of the green fluorescent protein in cell biology and biotechnology" *Nat. Biotechnol.* 15:961-964 (1997).

Motti et. al. "Recognition by Human Sera and Immunogenicity of HbsAg Mimotopes Selected form an M13 Phage Display Library," *Gene*, 146(2): 191-8, (1994).

Nolan et al. "Fluorescence-activated cell analysis and sorting of viable mammalian cells based on β-D-galactosidase activity after transduction of *Escherichia coli* lacZ", *Proc. Natl. Acad. Sci.* 85:2603-2607 (1988) U.S.A.

Nolan, G. P., Fiering, S. Nicolas, J.F.. & Herzenberg, L.A. "Fluorescence-activated cell analysis and sorting of viable mammalian cells based on beta-D galactosidase activity after transduction of *Escherichia coli* lacZ," *Proc, Natl. Acad. Sci.* U. S.S. N. No. S. A. 85, 2603-2607, (1988).

Oldenburg, K.R., Loganathan, D., Goldstein, I.J. Schultz, P.G. & Gallop, M.A. Peptide ligands for a sugar-binding protein isolated from a random peptide library, *Proc. Natl. Acad. Sci. U.S.A.* 89, 5393-5397, (1992).

Parmley, S.F. & Smith, G.P. "Antibody-selectable filamentous fd phage vectors: affinity purification of target genes," *Gene.* 73, 305-318, (1988).

Phalipon et. al. "Induction of Anti-Carbohydrate Antibodies by Phage Library-Selected peptides Miniics," *Eur. J. Immunol.* 27(10), 2620-5, (1997).

Rebar, E.J. & Pabo, C.O. "Zinc finger phage: affinity selection of fingers with new DNA-binding specificities," *Science* 263, 671-673, (1994).

Rebar, E.J., Greisman, H.A. & Pabo, C.O. "Phage display methods for selecting zinc finger proteins with novel DNA-binding specificities," *Methods Enzoymol.* 267, 129-149, (1996).

Roberts, R.W. & Szastack, J.W. "RNA-peptide fusions for the in vitro selection of peptides and proteins," *Proc. Natl. Acad. Sci. U.S.A.* 94, 12297-12302, (1997).

Saggio, i. & Laufer, R. "Biotin binders selected from a random peptide library expressed on phage," *Biochem. J.* 293, 613-616, (1993).

Schatz, P.J. "Use of peptide libraries to map the substrate specificity a peptide-modifying enzyme: a 13 residue consensus peptide specifies biotinylation in *Escherichia coli*," *Biotechnology* 11, 1138-1143, (1993).

Schatz, P.J., Cull, M.G., Martin, E.L. & Gates, C.M. "Screening of peptide libraries linked to lac repressor," *Methods Enzymol.* 267, 171-191, (1996).

Scott, J.K. & Smith, G.P. "Searching for peptide ligands with an epitope library," *Science* 249, 386-390, (1990).

Scott, J.K., Loganathan, D., Easley, R.B., Gong, X. & Goldstein, I.J. "A family of concanavalin A-binding peptides from a hexapeptide epitope library," *Proc. Natl. Acad. Sci. U.S.A.* 89, 5398-54-2, (1992).

Smith, G.P. "Filamentous fusion phage: novel expression vectors that display cloned antigens on the virion surface," *Science* 228, 1315-1317, (1985).

South et. al. "Identification of Novel Peptide Antagonists for Von Willebrand Factor Binding to the Platelet Glycoprotein 1b Receptor from a Phage Epitope Library," *Thromb. Haemost.* 73(1): 144-50, (1995).

Stoute et. al. "Induction of Humoral Immune Response against Plasmodium falciparum Sporozoites by Immunization with a synthetic Peptide Mimotope Whose Sequence was Derived from Screening a Filamentous Phage Epitope Library," *Infect. Immun.* 63(3): 934-9, (1995).

Wallace, et. al. "Selection of Potent Inhibitors of Farnesyl-Protein Trasferase from a Synthetic Tetrapeptide Combinatorial Library," *J. Bio. Chem.* 271(49), 31306-11, (1996).

Welsh and Kay. "Reporter gene expression for monitoring gene transfer", *Curr. Opin. Biotechnol.* 8:617-622 (1997).

Wennermers at. Al., "Peptide Complexation in Water. Sequence Selective Binding with Simple Dye Molecules," *Tetrahedron Letters*, 6413-6416, (1994).

Yu, J. & Smith, G.P. "Affinity maturation of phage-displayed peptide ligands," *Methods Enzymol*, 267, 3-27, (1996).

Zlokarnik et al. "Quantitation of transcription and clonal selection of single cells with β-lactamase as reporter", *Science*, 279:84-88 (1998).

Fluorescein carrier

Rhodamine Red carrier

Oregon Green 514 carrier

Texas Red carrier

Peptide - Texas Red Binding 0.5µM
Texas Red

A. Nonspecific peptide
GGGSKVILFEGPAG SGSAGSGAS GAPGSKVILFEGGPG HHHHHH

B. Pep. TR401 (linear)
KHVQYWTQMFYSGGGSAETVGGG HHHHHH

C. Pep. TRP501 (SKVILFE-flanked)
GGGSKVILFEGPAG RTIWEPKEASNHT GAPGSKVILFEGGPG HHHHHH D. Pep. TRP512 (SKVILFE-flanked)
GGGSKVILFEGPAG RWTWEPISE GAPGSKVILFEGGPG HHHHHH

SEQUENCE LISTING

<160> NUMBER OF SEQ ID NOS: 122

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 1

Lys His Val Gln Tyr Trp Thr Gln Met Phe Tyr Ser
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 2

Asp Phe Leu Gln Trp Lys Leu Ala Arg Gln Lys Pro
1               5                   10

<210> SEQ ID NO 3
<211> LENGTH: 12
<212> TYPE: PRT
<213> ORGANISM: Artificial Sequence
<220> FEATURE:

```
<223> OTHER INFORMATION: Description of Artificial Sequence: synthetic

<400> SEQUENCE: 3

Ile Pro His Pro Pro Met Tyr Trp Thr Arg Val Phe
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 4

His Gly Trp Asp Tyr Tyr Trp Asp Trp Thr Ala Trp
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 5

Ala Ser Asp Tyr Trp Asp Trp Glu Trp Tyr Tyr Ser
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 6

Tyr Pro Asn Asp Phe Glu Trp Trp Glu Tyr Tyr Phe
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 7

His Thr Ser His Ile Ser Trp Pro Pro Trp Tyr Phe
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 8

Leu Glu Pro Arg Trp Gly Phe Gly Trp Trp Leu Lys
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: synthetic
```

-continued

```
<400> SEQUENCE: 9

Gln Tyr Tyr Gly Trp Tyr Tyr Asp His Asn Phe Trp
 1               5                  10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 10

Tyr Met Tyr Asp Glu Tyr Gln Tyr Trp Asn Phe Trp
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 11

Trp Tyr Asp Asp Trp Asn Asp Trp His Ala Trp Pro
 1               5                  10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 12

Trp His Met Ser Pro Ser Trp Gly Trp Gly Tyr Trp
 1               5                  10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 13

His Met Ser Trp Trp Glu Phe Tyr Leu Val Pro Pro
 1               5                  10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 14

Tyr Trp Asp Tyr Ser Trp His Tyr Tyr Ala Pro Thr
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: synthetic
```

```
<400> SEQUENCE: 15

Lys Pro Val Gln Tyr Trp Thr Gln Met Phe Tyr Thr
  1               5                  10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence:  synthetic

<400> SEQUENCE: 16

Lys Pro Ala Gln Tyr Trp Thr Gln Met Phe Tyr Ser
  1               5                  10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence:  synthetic

<400> SEQUENCE: 17

Lys Asn Val Gln Tyr Trp Thr Gln Met Phe Tyr Thr
  1               5                  10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence:  synthetic

<400> SEQUENCE: 18

Lys His Val Gln Tyr Trp Thr His Met Phe Tyr Thr
  1               5                  10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence:  synthetic

<400> SEQUENCE: 19

Lys His Val Gln Tyr Trp Thr Gln Met Phe Tyr Thr
  1               5                  10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence:  synthetic

<400> SEQUENCE: 20

Asn His Val His Tyr Trp Thr Gln Met Phe Tyr Ser
  1               5                  10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence:  synthetic
```

```
<400> SEQUENCE: 21

Thr His Val Gln Tyr Trp Thr Gln Met Phe Tyr Ser
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 22

Ile Pro His Arg Pro Met Tyr Trp Thr Pro Val Phe
 1               5                  10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 23

Leu Pro His Pro Pro Met Tyr Trp Thr Arg Val Phe
 1               5                  10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 24

His Glu Trp Glu Tyr Tyr Trp Asp Trp Thr Ala Trp
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 25

His Glu Trp Asp Tyr Tyr Trp Asp Trp Thr Ala Trp
 1               5                  10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 26

His Gly Trp Asp Tyr Tyr Trp Asp Trp Thr Asp Trp
 1               5                  10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: synthetic
```

```
<400> SEQUENCE: 27

His Gly Trp Asp Tyr Tyr Trp Asp Trp Pro Thr Trp
  1               5                  10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence:  synthetic

<400> SEQUENCE: 28

His Gly Trp Asp Tyr Tyr Trp Asp Trp Thr Thr Trp
  1               5                  10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence:  synthetic

<400> SEQUENCE: 29

His Gly Trp Asp Tyr Asn Trp Asp Trp Thr Ala Trp
  1               5                  10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence:  synthetic

<400> SEQUENCE: 30

Gln Gly Trp Asp Tyr Tyr Trp Asp Trp Thr Ala Trp
  1               5                  10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence:  synthetic

<400> SEQUENCE: 31

Tyr Pro Asn Glu Phe Asp Trp Trp Asp Tyr Tyr Tyr
  1               5                  10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence:  synthetic

<400> SEQUENCE: 32

Tyr Pro Asn Asp Phe Glu Trp Trp Asp Tyr Tyr Tyr
  1               5                  10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence:  synthetic
```

<400> SEQUENCE: 33

Tyr His Asn Asp Tyr Glu Trp Trp Glu Tyr Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 34

Tyr Pro Asn Asp Phe Glu Trp Trp Glu Tyr Tyr Tyr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 35

Tyr Pro Asn Asp Phe Asp Trp Trp Glu Tyr Tyr Leu
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 36

Tyr Thr His Asp Tyr Glu Trp Trp Glu Tyr Tyr Phe
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 37

Tyr Pro Asn Asp Tyr Glu Trp Trp Glu Tyr Tyr Phe
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 38

Tyr Pro Asp Ser Phe Glu Trp Trp Glu Tyr Tyr Phe
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: synthetic

```
<400> SEQUENCE: 39

Tyr His Asp Phe Glu Trp Trp Glu Tyr Tyr Phe
 1               5                  10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence:  synthetic

<400> SEQUENCE: 40

Tyr Pro Tyr Asp Phe Glu Trp Trp Glu Tyr Tyr Met
 1               5                  10

<210> SEQ ID NO 41
<211> LENGTH: 29
<212> TYPE: PRT
<213> ORGANISM: Artificial Sequence
<220> FEATURE:
<223> OTHER INFORMATION: Description of Artificial Sequence:  synthetic

<400> SEQUENCE: 41

Lys His Val Gln Tyr Trp Thr Gln Met Phe Tyr Ser Gly Gly Gly Ser
 1               5                  10                  15

Ala Glu Thr Val Gly Gly Gly His His His His His His
            20                  25

<210> SEQ ID NO 42
<211> LENGTH: 29
<212> TYPE: PRT
<213> ORGANISM: Artificial Sequence
<220> FEATURE:
<223> OTHER INFORMATION: Description of Artificial Sequence:  synthetic

<400> SEQUENCE: 42

Lys Pro Val Gln Tyr Trp Thr Gln Met Phe Tyr Thr Gly Gly Gly Ser
 1               5                  10                  15

Ala Glu Thr Val Gly Gly Gly His His His His His His
            20                  25

<210> SEQ ID NO 43
<211> LENGTH: 29
<212> TYPE: PRT
<213> ORGANISM: Artificial Sequence
<220> FEATURE:
<223> OTHER INFORMATION: Description of Artificial Sequence:  synthetic

<400> SEQUENCE: 43

Asp Phe Leu Gln Trp Lys Leu Ala Arg Gln Lys Pro Gly Gly Gly Ser
 1               5                  10                  15

Ala Glu Thr Val Gly Gly Gly His His His His His His
            20                  25

<210> SEQ ID NO 44
<211> LENGTH: 29
<212> TYPE: PRT
<213> ORGANISM: Artificial Sequence
<220> FEATURE:
<223> OTHER INFORMATION: Description of Artificial Sequence:  synthetic

<400> SEQUENCE: 44

His Gly Trp Asp Tyr Tyr Trp Asp Trp Thr Ala Trp Gly Gly Gly Ser
 1               5                  10                  15
```

-continued

Ala Glu Thr Val Gly Gly Gly His His His His His His
            20                  25

<210> SEQ ID NO 45
<211> LENGTH: 29
<212> TYPE: PRT
<213> ORGANISM: Artificial Sequence
<220> FEATURE:
<223> OTHER INFORMATION: Description of Artificial Sequence: synthetic

<400> SEQUENCE: 45

Ala Ser Asp Tyr Trp Asp Trp Glu Trp Tyr Tyr Ser Gly Gly Gly Ser
 1               5                  10                  15

Ala Glu Thr Val Gly Gly Gly His His His His His His
            20                  25

<210> SEQ ID NO 46
<211> LENGTH: 29
<212> TYPE: PRT
<213> ORGANISM: Artificial Sequence
<220> FEATURE:
<223> OTHER INFORMATION: Description of Artificial Sequence: synthetic

<400> SEQUENCE: 46

Tyr Pro Asn Asp Phe Glu Trp Trp Glu Tyr Tyr Phe Gly Gly Gly Ser
 1               5                  10                  15

Ala Glu Thr Val Gly Gly Gly His His His His His His
            20                  25

<210> SEQ ID NO 47
<211> LENGTH: 29
<212> TYPE: PRT
<213> ORGANISM: Artificial Sequence
<220> FEATURE:
<223> OTHER INFORMATION: Description of Artificial Sequence: synthetic

<400> SEQUENCE: 47

Tyr Pro Asn Glu Phe Asp Trp Trp Asp Tyr Tyr Tyr Gly Gly Gly Ser
 1               5                  10                  15

Ala Glu Thr Val Gly Gly Gly His His His His His His
            20                  25

<210> SEQ ID NO 48
<211> LENGTH: 29
<212> TYPE: PRT
<213> ORGANISM: Artificial Sequence
<220> FEATURE:
<223> OTHER INFORMATION: Description of Artificial Sequence: synthetic

<400> SEQUENCE: 48

Ala Ser Gly Ser Gly Ala Ser Gly Ser Ala Gly Ser Gly Gly Gly Ser
 1               5                  10                  15

Ala Glu Thr Val Gly Gly Gly His His His His His His
            20                  25

<210> SEQ ID NO 49
<211> LENGTH: 60
<212> TYPE: PRT
<213> ORGANISM: Artificial Sequence
<220> FEATURE:
<221> NAME/KEY: UNSURE
<222> LOCATION: (28)..(33)
<223> OTHER INFORMATION: The x at positions 28 through 33 represents any
      amino acid residue.
<220> FEATURE:
<223> OTHER INFORMATION: Description of Artificial Sequence: synthetic

```
<400> SEQUENCE: 49

Met Gly Cys Ala Ala Leu Glu Ser Glu Val Ser Ala Leu Glu Ser Glu
1               5                   10                  15

Val Ala Ser Leu Glu Ser Glu Val Ala Ala Leu Xaa Xaa Xaa Xaa Xaa
            20                  25                  30

Xaa Leu Ala Ala Val Lys Ser Lys Leu Ser Ala Val Lys Ser Leu Ala
        35                  40                  45

Ser Val Lys Ser Lys Leu Ala Ala Cys Gly Pro Pro
    50                  55                  60

<210> SEQ ID NO 50
<211> LENGTH: 67
<212> TYPE: PRT
<213> ORGANISM: Artificial Sequence
<220> FEATURE:
<223> OTHER INFORMATION: Description of Artificial Sequence: synthetic

<400> SEQUENCE: 50

Met Gly Arg Asn Ser Gln Ala Thr Ser Gly Phe Thr Phe Ser His Phe
1               5                   10                  15

Tyr Met Glu Trp Trp Arg Gly Gly Glu Tyr Ile Ala Ala Ser Arg His
            20                  25                  30

Lys His Asn Lys Tyr Thr Thr Glu Tyr Ser Ala Ser Val Lys Gly Arg
        35                  40                  45

Tyr Ile Val Ser Arg Asp Thr Ser Gln Ser Ile Leu Tyr Gln Lys Lys
    50                  55                  60

Gly Pro Pro
 65

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: synthetic

<400> SEQUENCE: 51

Ser Lys Val Ile Leu Phe
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: synthetic

<400> SEQUENCE: 52

Ser Lys Val Ile Leu Phe Glu
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: synthetic

<400> SEQUENCE: 53

Ser Lys Val Ile Leu Phe Asp
1               5
```

-continued

```
<210> SEQ ID NO 54
<211> LENGTH: 7
<212> TYPE: PRT
<213> ORGANISM: Monkey virus

<400> SEQUENCE: 54

Pro Lys Lys Lys Arg Lys Val
 1               5

<210> SEQ ID NO 55
<211> LENGTH: 6
<212> TYPE: PRT
<213> ORGANISM: Homo sapiens

<400> SEQUENCE: 55

Ala Arg Arg Arg Arg Pro
 1               5

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: synthetic

<400> SEQUENCE: 56

Glu Glu Val Gln Arg Lys Arg Gln Lys Leu
 1               5                  10

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: synthetic

<400> SEQUENCE: 57

Glu Glu Lys Arg Lys Arg Thr Tyr Glu
 1               5

<210> SEQ ID NO 58
<211> LENGTH: 20
<212> TYPE: PRT
<213> ORGANISM: Xenopus

<400> SEQUENCE: 58

Ala Val Lys Arg Pro Ala Ala Thr Lys Lys Ala Gly Gln Ala Lys Lys
 1               5                  10                  15

Lys Lys Leu Asp
            20

<210> SEQ ID NO 59
<211> LENGTH: 31
<212> TYPE: PRT
<213> ORGANISM: Artificial Sequence
<220> FEATURE:
<223> OTHER INFORMATION: Description of Artificial Sequence: synthetic

<400> SEQUENCE: 59

Met Ala Ser Pro Leu Thr Arg Phe Leu Ser Leu Asn Leu Leu Leu Leu
 1               5                  10                  15

Gly Glu Ser Ile Leu Gly Ser Gly Glu Ala Lys Pro Gln Ala Pro
            20                  25                  30
```

```
<210> SEQ ID NO 60
<211> LENGTH: 21
<212> TYPE: PRT
<213> ORGANISM: Artificial Sequence
<220> FEATURE:
<223> OTHER INFORMATION: Description of Artificial Sequence: synthetic

<400> SEQUENCE: 60

Met Ser Ser Phe Gly Tyr Arg Thr Leu Thr Val Ala Leu Phe Thr Leu
 1               5                  10                  15

Ile Cys Cys Pro Gly
             20

<210> SEQ ID NO 61
<211> LENGTH: 51
<212> TYPE: PRT
<213> ORGANISM: Artificial Sequence
<220> FEATURE:
<223> OTHER INFORMATION: Description of Artificial Sequence: synthetic

<400> SEQUENCE: 61

Pro Gln Arg Pro Glu Asp Cys Arg Pro Arg Gly Ser Val Lys Gly Thr
 1               5                  10                  15

Gly Leu Asp Phe Ala Cys Asp Ile Tyr Ile Trp Ala Pro Leu Ala Gly
             20                  25                  30

Ile Cys Val Ala Leu Leu Leu Ser Leu Ile Ile Thr Leu Ile Cys Tyr
         35                  40                  45

His Ser Arg
     50

<210> SEQ ID NO 62
<211> LENGTH: 33
<212> TYPE: PRT
<213> ORGANISM: Artificial Sequence
<220> FEATURE:
<223> OTHER INFORMATION: Description of Artificial Sequence: synthetic

<400> SEQUENCE: 62

Met Val Ile Ile Val Thr Val Val Ser Val Leu Leu Ser Leu Phe Val
 1               5                  10                  15

Thr Ser Val Leu Leu Cys Phe Ile Phe Gly Gln His Leu Arg Gln Gln
             20                  25                  30

Arg

<210> SEQ ID NO 63
<211> LENGTH: 35
<212> TYPE: PRT
<213> ORGANISM: Artificial Sequence
<220> FEATURE:
<223> OTHER INFORMATION: Description of Artificial Sequence: synthetic

<400> SEQUENCE: 63

Pro Asn Lys Gly Ser Gly Thr Thr Ser Gly Thr Thr Arg Leu Leu Ser
 1               5                  10                  15

Gly His Cys Phe Thr Leu Thr Gly Leu Leu Gly Thr Val Thr Met Gly
             20                  25                  30

Leu Leu Thr
         35

<210> SEQ ID NO 64
<211> LENGTH: 14
<212> TYPE: PRT
<213> ORGANISM: Artificial Sequence
```

```
<220> FEATURE:
<223> OTHER INFORMATION: Description of Artificial Sequence:  synthetic

<400> SEQUENCE: 64

Met Gly Ser Ser Lys Ser Lys Pro Lys Asp Pro Ser Gln Arg
 1               5                  10

<210> SEQ ID NO 65
<211> LENGTH: 26
<212> TYPE: PRT
<213> ORGANISM: Artificial Sequence
<220> FEATURE:
<223> OTHER INFORMATION: Description of Artificial Sequence:  synthetic

<400> SEQUENCE: 65

Leu Leu Gln Arg Leu Phe Ser Arg Gln Asp Cys Cys Gly Asn Cys Ser
 1               5                  10                  15

Asp Ser Glu Glu Glu Leu Pro Thr Arg Leu
            20                  25

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence:  synthetic

<400> SEQUENCE: 66

Lys Gln Phe Arg Asn Cys Met Leu Thr Ser Leu Cys Cys Gly Lys Asn
 1               5                  10                  15

Pro Leu Gly Asp
            20

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence:  synthetic

<400> SEQUENCE: 67

Leu Asn Pro Pro Asp Glu Ser Gly Pro Gly Cys Met Ser Cys Lys Cys
 1               5                  10                  15

Val Leu Ser

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence:  synthetic

<400> SEQUENCE: 68

Lys Phe Glu Arg Gln
 1               5

<210> SEQ ID NO 69
<211> LENGTH: 36
<212> TYPE: PRT
<213> ORGANISM: Artificial Sequence
<220> FEATURE:
<223> OTHER INFORMATION: Description of Artificial Sequence:  synthetic

<400> SEQUENCE: 69

Met Leu Ile Pro Ile Ala Gly Phe Phe Ala Leu Ala Gly Leu Val Leu
```

-continued

```
                 1               5              10              15
Ile Val Leu Ile Ala Tyr Leu Ile Gly Arg Lys Arg Ser His Ala Gly
                20              25              30

Tyr Gln Thr Ile
        35

<210> SEQ ID NO 70
<211> LENGTH: 35
<212> TYPE: PRT
<213> ORGANISM: Artificial Sequence
<220> FEATURE:
<223> OTHER INFORMATION: Description of Artificial Sequence:  synthetic

<400> SEQUENCE: 70

Leu Val Pro Ile Ala Val Gly Ala Ala Leu Ala Gly Val Leu Ile Leu
 1               5              10              15

Val Leu Leu Ala Tyr Phe Ile Gly Leu Lys His His His Ala Gly Tyr
                20              25              30

Glu Gln Phe
        35

<210> SEQ ID NO 71
<211> LENGTH: 26
<212> TYPE: PRT
<213> ORGANISM: Yeast

<400> SEQUENCE: 71

Met Leu Arg Thr Ser Ser Leu Phe Thr Arg Arg Val Gln Pro Ser Leu
 1               5              10              15

Phe Ser Arg Asn Ile Leu Arg Gln Ser Thr
                20              25

<210> SEQ ID NO 72
<211> LENGTH: 25
<212> TYPE: PRT
<213> ORGANISM: Yeast

<400> SEQUENCE: 72

Met Leu Ser Leu Arg Gln Ser Ile Arg Phe Phe Lys Pro Ala Thr Arg
 1               5              10              15

Thr Leu Cys Ser Ser Arg Tyr Leu Leu
                20              25

<210> SEQ ID NO 73
<211> LENGTH: 64
<212> TYPE: PRT
<213> ORGANISM: Yeast

<400> SEQUENCE: 73

Met Phe Ser Met Leu Ser Lys Arg Trp Ala Gln Arg Thr Leu Ser Lys
 1               5              10              15

Ser Phe Tyr Ser Thr Ala Thr Gly Ala Ala Ser Lys Ser Gly Lys Leu
                20              25              30

Thr Gln Lys Leu Val Thr Ala Gly Val Ala Ala Ala Gly Ile Thr Ala
        35              40              45

Ser Thr Leu Leu Tyr Ala Asp Ser Leu Thr Ala Glu Ala Met Thr Ala
        50              55              60

<210> SEQ ID NO 74
<211> LENGTH: 41
<212> TYPE: PRT
```

<213> ORGANISM: Yeast

<400> SEQUENCE: 74

Met Lys Ser Phe Ile Thr Arg Asn Lys Thr Ala Ile Leu Ala Thr Val
1               5                   10                  15

Ala Ala Thr Gly Thr Ala Ile Gly Ala Tyr Tyr Tyr Asn Gln Leu
            20                  25                  30

Gln Gln Gln Gln Gln Arg Gly Lys Lys
        35                  40

<210> SEQ ID NO 75
<211> LENGTH: 15
<212> TYPE: PRT
<213> ORGANISM: Adenovirus

<400> SEQUENCE: 75

Leu Tyr Leu Ser Arg Arg Ser Phe Ile Asp Glu Lys Lys Met Pro
1               5                   10                  15

<210> SEQ ID NO 76
<211> LENGTH: 19
<212> TYPE: PRT
<213> ORGANISM: Artificial Sequence
<220> FEATURE:
<223> OTHER INFORMATION: Description of Artificial Sequence: synthetic

<400> SEQUENCE: 76

Leu Asn Pro Pro Asp Glu Ser Gly Pro Gly Cys Met Ser Cys Lys Cys
1               5                   10                  15

Val Leu Ser

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: synthetic

<400> SEQUENCE: 77

Leu Thr Glu Pro Thr Gln Pro Thr Arg Asn Gln Cys Cys Ser Asn
1               5                   10                  15

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: synthetic

<400> SEQUENCE: 78

Arg Thr Ala Leu Gly Asp Ile Gly Asn
1               5

<210> SEQ ID NO 79
<211> LENGTH: 20
<212> TYPE: PRT
<213> ORGANISM: Artificial Sequence
<220> FEATURE:
<223> OTHER INFORMATION: Description of Artificial Sequence: synthetic

<400> SEQUENCE: 79

Met Tyr Arg Met Gln Leu Leu Ser Cys Ile Ala Leu Ser Leu Ala Leu
1               5                   10                  15

Val Thr Asn Ser

<210> SEQ ID NO 80
<211> LENGTH: 29
<212> TYPE: PRT
<213> ORGANISM: Artificial Sequence
<220> FEATURE:
<223> OTHER INFORMATION: Description of Artificial Sequence: synthetic

<400> SEQUENCE: 80

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr
            20                  25

<210> SEQ ID NO 81
<211> LENGTH: 27
<212> TYPE: PRT
<213> ORGANISM: Prepoinsulin

<400> SEQUENCE: 81

Met Ala Leu Trp Met Arg Leu Leu Pro Leu Leu Ala Leu Leu Ala Leu
 1               5                  10                  15

Trp Gly Pro Asp Pro Ala Ala Ala Phe Val Asn
            20                  25

<210> SEQ ID NO 82
<211> LENGTH: 18
<212> TYPE: PRT
<213> ORGANISM: Influenza

<400> SEQUENCE: 82

Met Lys Ala Lys Leu Leu Val Leu Leu Tyr Ala Phe Val Ala Gly Asp
 1               5                  10                  15

Gln Ile

<210> SEQ ID NO 83
<211> LENGTH: 24
<212> TYPE: PRT
<213> ORGANISM: Artificial Sequence
<220> FEATURE:
<223> OTHER INFORMATION: Description of Artificial Sequence: synthetic

<400> SEQUENCE: 83

Met Gly Leu Thr Ser Gln Leu Leu Pro Pro Leu Phe Phe Leu Leu Ala
 1               5                  10                  15

Cys Ala Gly Asn Phe Val His Gly
            20

<210> SEQ ID NO 84
<211> LENGTH: 14
<212> TYPE: PRT
<213> ORGANISM: Artificial Sequence
<220> FEATURE:
<221> NAME/KEY: UNSURE
<222> LOCATION: (3)..(10)
<223> OTHER INFORMATION: The x at positions 3 through 10 represents a
      fluorotte of any amino acid.
<220> FEATURE:
<223> OTHER INFORMATION: Description of Artificial Sequence: synthetic

<400> SEQUENCE: 84

Met Gly Xaa Xaa Xaa Xaa Xaa Xaa Xaa Xaa Gly Gly Pro Pro
 1               5                  10

```
<210> SEQ ID NO 85
<211> LENGTH: 2
<212> TYPE: PRT
<213> ORGANISM: Artificial Sequence
<220> FEATURE:
<223> OTHER INFORMATION: Description of Artificial Sequence: synthetic

<400> SEQUENCE: 85

Gly Ser
  1

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: synthetic

<400> SEQUENCE: 86

Gly Ser Gly Gly Ser
  1               5

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 87

Gly Gly Gly Ser
  1

<210> SEQ ID NO 88
<211> LENGTH: 90
<212> TYPE: DNA
<213> ORGANISM: Artificial Sequence
<220> FEATURE:
<223> OTHER INFORMATION: Description of Artificial Sequence: synthetic

<400> SEQUENCE: 88
ctccccttcg gccgaacctc caccagaata aacatctgc gtccaatact gcacatgctt          60
agagtgagaa tagaaaggta ccactctccc                                         90

<210> SEQ ID NO 89
<211> LENGTH: 90
<212> TYPE: DNA
<213> ORGANISM: Artificial Sequence
<220> FEATURE:
<223> OTHER INFORMATION: Description of Artificial Sequence: synthetic

<400> SEQUENCE: 89
ctccccttcg gccgaacctc caccaaacac acgagtccaa tacataggag gatgcggaat        60
agagtgagaa tagaaaggta ccactctccc                                         90

<210> SEQ ID NO 90
<211> LENGTH: 90
<212> TYPE: PRT
<213> ORGANISM: Artificial Sequence
<220> FEATURE:
<223> OTHER INFORMATION: Description of Artificial Sequence: synthetic

<400> SEQUENCE: 90

Cys Thr Cys Cys Cys Cys Thr Thr Cys Gly Gly Cys Cys Gly Ala Ala
  1               5                  10                  15
```

Cys Cys Thr Cys Cys Ala Cys Cys Ala Ala Ala Thr Ala Ala Thr
                20                  25                  30

Ala Cys Thr Cys Cys Ala Cys Cys Ala Cys Thr Cys Ala Ala Ala
            35                  40                  45

Ala Thr Cys Ala Thr Thr Cys Gly Gly Ala Thr Ala Ala Gly Ala Gly
    50                  55                  60

Thr Gly Ala Gly Ala Ala Thr Ala Gly Ala Ala Ala Gly Gly Thr Ala
65                  70                  75                  80

Cys Cys Ala Cys Thr Cys Thr Cys Cys Cys
            85                  90

<210> SEQ ID NO 91
<211> LENGTH: 90
<212> TYPE: DNA
<213> ORGANISM: Artificial Sequence
<220> FEATURE:
<223> OTHER INFORMATION: Description of Artificial Sequence: synthetic

<400> SEQUENCE: 91
ctccccttcg gccgaacctc caccccaagc agtccaatcc caataataat cccacccatg      60
agagtgagaa tagaaaggta ccactctccc                                      90

<210> SEQ ID NO 92
<211> LENGTH: 27
<212> TYPE: DNA
<213> ORGANISM: Artificial Sequence
<220> FEATURE:
<223> OTHER INFORMATION: Description of Artificial Sequence: synthetic

<400> SEQUENCE: 92
gggagagtgg tacctttcta ttctcac                                         27

<210> SEQ ID NO 93
<211> LENGTH: 42
<212> TYPE: PRT
<213> ORGANISM: Artificial Sequence
<220> FEATURE:
<221> NAME/KEY: UNSURE
<222> LOCATION: (15)..(27)
<223> OTHER INFORMATION: The x at positions 15 through 27 represents any
      amino acid.
<220> FEATURE:
<223> OTHER INFORMATION: Description of Artificial Sequence: synthetic

<400> SEQUENCE: 93

Gly Gly Gly Ser Lys Val Ile Leu Phe Glu Gly Pro Ala Gly Xaa Xaa
1               5                   10                  15

Xaa Xaa Xaa Xaa Xaa Xaa Xaa Xaa Xaa Xaa Xaa Gly Ala Pro Gly Ser
            20                  25                  30

Lys Val Ile Leu Phe Glu Gly Gly Pro Gly
        35                  40

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 94

Gly Pro Ala Gly
1

```
<210> SEQ ID NO 95
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 95

Gly Ala Pro Gly
  1

<210> SEQ ID NO 96
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 96

Gly Gly Pro Gly
  1

<210> SEQ ID NO 97
<211> LENGTH: 42
<212> TYPE: PRT
<213> ORGANISM: Artificial Sequence
<220> FEATURE:
<223> OTHER INFORMATION: Description of Artificial Sequence: synthetic

<400> SEQUENCE: 97

Gly Gly Gly Ser Lys Val Ile Leu Phe Glu Gly Pro Ala Gly Arg Thr
  1               5                  10                  15

Ile Trp Glu Pro Lys Glu Ala Ser Asn His Thr Gly Ala Pro Gly Ser
             20                  25                  30

Lys Val Ile Leu Phe Glu Gly Gly Pro Gly
         35                  40

<210> SEQ ID NO 98
<211> LENGTH: 38
<212> TYPE: PRT
<213> ORGANISM: Artificial Sequence
<220> FEATURE:
<223> OTHER INFORMATION: Description of Artificial Sequence: synthetic

<400> SEQUENCE: 98

Gly Gly Gly Ser Lys Val Ile Leu Phe Glu Gly Pro Ala Gly Trp Ser
  1               5                  10                  15

Lys Met Gly His Thr Val Thr Gly Ala Pro Gly Ser Lys Val Ile Leu
             20                  25                  30

Phe Glu Gly Gly Pro Gly
         35

<210> SEQ ID NO 99
<211> LENGTH: 38
<212> TYPE: PRT
<213> ORGANISM: Artificial Sequence
<220> FEATURE:
<223> OTHER INFORMATION: Description of Artificial Sequence: synthetic

<400> SEQUENCE: 99

Gly Gly Gly Ser Lys Val Ile Leu Phe Glu Gly Pro Ala Gly Arg Trp
  1               5                  10                  15

Thr Trp Glu Pro Ile Ser Glu Gly Ala Pro Gly Ser Lys Val Ile Leu
             20                  25                  30
```

Phe Glu Gly Gly Pro Gly
        35

<210> SEQ ID NO 100
<211> LENGTH: 42
<212> TYPE: PRT
<213> ORGANISM: Artificial Sequence
<220> FEATURE:
<223> OTHER INFORMATION: Description of Artificial Sequence: synthetic

<400> SEQUENCE: 100

Gly Gly Gly Ser Lys Val Ile Leu Phe Glu Gly Pro Ala Gly Gly Asn
1               5                   10                  15

Gln Lys Cys Leu Gln His Asn Arg Cys Ser Thr Gly Ala Pro Gly Ser
            20                  25                  30

Lys Val Ile Leu Phe Glu Gly Gly Pro Gly
        35                  40

<210> SEQ ID NO 101
<211> LENGTH: 38
<212> TYPE: PRT
<213> ORGANISM: Artificial Sequence
<220> FEATURE:
<223> OTHER INFORMATION: Description of Artificial Sequence: synthetic

<400> SEQUENCE: 101

Gly Gly Gly Ser Lys Val Ile Leu Phe Glu Gly Pro Ala Gly Ser Gln
1               5                   10                  15

Thr Trp Ser Phe Pro Glu His Gly Ala Pro Gly Ser Lys Val Ile Leu
            20                  25                  30

Phe Glu Gly Gly Pro Gly
        35

<210> SEQ ID NO 102
<211> LENGTH: 42
<212> TYPE: PRT
<213> ORGANISM: Artificial Sequence
<220> FEATURE:
<223> OTHER INFORMATION: Description of Artificial Sequence: synthetic

<400> SEQUENCE: 102

Gly Gly Gly Ser Lys Val Ile Leu Phe Glu Gly Pro Ala Gly Glu Pro
1               5                   10                  15

Met Ala Arg Pro Trp Glu Arg Lys Gln Asp Arg Gly Ala Pro Gly Ser
            20                  25                  30

Lys Val Ile Leu Phe Glu Gly Gly Pro Gly
        35                  40

<210> SEQ ID NO 103
<211> LENGTH: 42
<212> TYPE: PRT
<213> ORGANISM: Artificial Sequence
<220> FEATURE:
<223> OTHER INFORMATION: Description of Artificial Sequence: synthetic

<400> SEQUENCE: 103

Gly Gly Gly Ser Lys Val Ile Leu Phe Glu Gly Pro Ala Gly Gly Thr
1               5                   10                  15

Leu Ser Ala Thr Arg Pro Tyr Gly Arg Gln Trp Gly Ala Pro Gly Ser
            20                  25                  30

Lys Val Ile Leu Phe Glu Gly Gly Pro Gly
        35                  40

```
<210> SEQ ID NO 104
<211> LENGTH: 6
<212> TYPE: PRT
<213> ORGANISM: Artificial Sequence
<220> FEATURE:
<221> NAME/KEY: UNSURE
<222> LOCATION: (2)..(3)
<223> OTHER INFORMATION: The x at positions 2 and 3 represents any amino
      acid.
<220> FEATURE:
<223> OTHER INFORMATION: Description of Artificial Sequence: synthetic

<400> SEQUENCE: 104

Arg Xaa Xaa Trp Glu Pro
 1               5

<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence: synthetic

<400> SEQUENCE: 105

Arg Thr Ile Trp Glu Pro Lys Glu Ala Ser Asn His Thr
 1               5                  10

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: synthetic

<400> SEQUENCE: 106

Trp Ser Lys Met Gly His Thr Val Thr
 1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: synthetic

<400> SEQUENCE: 107

Arg Trp Thr Trp Glu Pro Ile Ser Glu
 1               5

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence: synthetic

<400> SEQUENCE: 108

Gly Asn Gln Lys Cys Leu Gln His Asn Arg Cys Ser Thr
 1               5                  10

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: synthetic
```

```
<400> SEQUENCE: 109

Ser Gln Thr Trp Ser Phe Pro Glu His
 1               5

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: synthetic

<400> SEQUENCE: 110

Glu Pro Met Ala Arg Pro Trp Glu Arg Lys Gln Asp Arg
 1               5                  10

<210> SEQ ID NO 111
<211> LENGTH: 13
<212> TYPE: PRT
<213> ORGANISM: Artificial Sequence
<220> FEATURE:
<223> OTHER INFORMATION: Description of Artificial Sequence: synthetic

<400> SEQUENCE: 111

Gly Leu Thr Ser Ala Thr Arg Pro Tyr Gly Arg Gln Trp
 1               5                  10

<210> SEQ ID NO 112
<211> LENGTH: 22
<212> TYPE: PRT
<213> ORGANISM: Artificial Sequence
<220> FEATURE:
<221> NAME/KEY: UNSURE
<222> LOCATION: (7)
<223> OTHER INFORMATION: The x at position 7 represents either Glutamic
      acid or Aspartic acid.
<220> FEATURE:
<221> NAME/KEY: UNSURE
<222> LOCATION: (8)..(15)
<223> OTHER INFORMATION: The x at positions 8 through 15 represents any
      amino acid.
<220> FEATURE:
<221> NAME/KEY: UNSURE
<222> LOCATION: (22)
<223> OTHER INFORMATION: The x at position 22 represents either Glutamic
      acid or Aspartic acid.
<220> FEATURE:
<223> OTHER INFORMATION: Description of Artificial Sequence: synthetic

<400> SEQUENCE: 112

Ser Lys Val Ile Leu Phe Xaa Xaa Xaa Xaa Xaa Xaa Xaa Xaa Ser
 1               5                  10                  15

Lys Val Ile Leu Phe Xaa
             20

<210> SEQ ID NO 113
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 113

Tyr Trp Asp Trp
 1

<210> SEQ ID NO 114
<211> LENGTH: 4
<212> TYPE: PRT
```

```
<213> ORGANISM: Artificial Sequence
<220> FEATURE:
<221> NAME/KEY: UNSURE
<222> LOCATION: (2)
<223> OTHER INFORMATION: The x at position 2 represents either Aspartic
      acid or Glutamic acid.
<220> FEATURE:
<223> OTHER INFORMATION: Description of Artificial Sequence: synthetic

<400> SEQUENCE: 114

Trp Xaa Tyr Tyr
 1

<210> SEQ ID NO 115
<211> LENGTH: 20
<212> TYPE: PRT
<213> ORGANISM: Artificial Sequence
<220> FEATURE:
<223> OTHER INFORMATION: Description of Artificial Sequence: synthetic

<400> SEQUENCE: 115

Cys Cys Cys Thr Cys Ala Thr Ala Gly Thr Thr Ala Gly Cys Gly Thr
 1               5                  10                  15

Ala Ala Cys Gly
            20

<210> SEQ ID NO 116
<211> LENGTH: 12
<212> TYPE: PRT
<213> ORGANISM: Artificial Sequence
<220> FEATURE:
<221> NAME/KEY: UNSURE
<222> LOCATION: (1)
<223> OTHER INFORMATION: The xaa at position 1 represents either Lysine,
      Asparagine or Threonine.
<220> FEATURE:
<221> NAME/KEY: UNSURE
<222> LOCATION: (2)
<223> OTHER INFORMATION: The xaa at position 2 represents either
      Histidine,
      Proline or Asparagine.
<220> FEATURE:
<221> NAME/KEY: UNSURE
<222> LOCATION: (3)
<223> OTHER INFORMATION: The xaa at position 3 represents either Alanine
      or Valine.
<220> FEATURE:
<221> NAME/KEY: UNSURE
<222> LOCATION: (4)
<223> OTHER INFORMATION: The xaa at position 4 represents either
      Histidine or Glutamine.
<220> FEATURE:
<221> NAME/KEY: UNSURE
<222> LOCATION: (8)
<223> OTHER INFORMATION: The xaa at position 8 represents either
      Histidine or Glutamine.
<220> FEATURE:
<221> NAME/KEY: UNSURE
<222> LOCATION: (12)
<223> OTHER INFORMATION: The xaa at position 12 represents either Serine
      or Threonine.
<220> FEATURE:
<223> OTHER INFORMATION: Description of Artificial Sequence: synthetic

<400> SEQUENCE: 116

Xaa Xaa Xaa Xaa Tyr Trp Thr Xaa Met Phe Tyr Xaa
 1               5                  10

<210> SEQ ID NO 117
<211> LENGTH: 12
<212> TYPE: PRT
<213> ORGANISM: Artificial Sequence
```

```
<220> FEATURE:
<221> NAME/KEY: UNSURE
<222> LOCATION: (1)
<223> OTHER INFORMATION: The xaa at position 1 represents either
      Isoleucine or Leucine.
<220> FEATURE:
<221> NAME/KEY: UNSURE
<222> LOCATION: (4)
<223> OTHER INFORMATION: The xaa at position 4 represents either Proline
      or Arginine.
<220> FEATURE:
<221> NAME/KEY: UNSURE
<222> LOCATION: (10)
<223> OTHER INFORMATION: The xaa at position 10 represents either
      Proline or Arginine.
<220> FEATURE:
<223> OTHER INFORMATION: Description of Artificial Sequence:   synthetic

<400> SEQUENCE: 117

Xaa Pro His Xaa Pro Met Tyr Trp Thr Xaa Val Phe
 1               5                   10

<210> SEQ ID NO 118
<211> LENGTH: 13
<212> TYPE: PRT
<213> ORGANISM: Artificial Sequence
<220> FEATURE:
<221> NAME/KEY: UNSURE
<222> LOCATION: (1)
<223> OTHER INFORMATION: The xaa at position 1 represents either
      Histidine or Glutamine.
<220> FEATURE:
<221> NAME/KEY: UNSURE
<222> LOCATION: (2)
<223> OTHER INFORMATION: The xaa at position 2 represents either
      Glutamic acid or Glycine.
<220> FEATURE:
<221> NAME/KEY: UNSURE
<222> LOCATION: (4)
<223> OTHER INFORMATION: The xaa at position 4 represents either
      Aspartic acid or Glutamic acid.
<220> FEATURE:
<221> NAME/KEY: UNSURE
<222> LOCATION: (6)
<223> OTHER INFORMATION: The xaa at position 6 represents either
      Tyrosine or Asparagine.
<220> FEATURE:
<221> NAME/KEY: UNSURE
<222> LOCATION: (11)
<223> OTHER INFORMATION: The xaa at position 11 represents either
      Alanine, Aspartic acid, Proline or Threonine.
<220> FEATURE:
<223> OTHER INFORMATION: Description of Artificial Sequence:   synthetic

<400> SEQUENCE: 118

Xaa Xaa Trp Xaa Tyr Xaa Trp Asp Trp Thr Xaa Phe Trp
 1               5                   10

<210> SEQ ID NO 119
<211> LENGTH: 12
<212> TYPE: PRT
<213> ORGANISM: Artificial Sequence
<220> FEATURE:
<221> NAME/KEY: UNSURE
<222> LOCATION: (2)
<223> OTHER INFORMATION: The xaa at position 2 represents either
      Histidine, Proline, Threonine or is optionally omitted.
<220> FEATURE:
<221> NAME/KEY: UNSURE
<222> LOCATION: (3)
<223> OTHER INFORMATION: The xaa at position 3 represents either
      Histidine, Asparagine, Serine or Tyrosine.
<220> FEATURE:
<221> NAME/KEY: UNSURE
<222> LOCATION: (4)
```

```
<223> OTHER INFORMATION: The xaa at position 4 represents either
      Aspartic acid or Glutamic acid.
<220> FEATURE:
<221> NAME/KEY: UNSURE
<222> LOCATION: (5)
<223> OTHER INFORMATION: The xaa at position 5 represents either
      Phenylalanine or Tyrosine.
<220> FEATURE:
<221> NAME/KEY: UNSURE
<222> LOCATION: (6)
<223> OTHER INFORMATION: The xaa at position 6 presents either Aspartic
      acid or Glutamic acid.
<220> FEATURE:
<221> NAME/KEY: UNSURE
<222> LOCATION: (9)
<223> OTHER INFORMATION: The xaa at position 9 represents either
      Aspartic acid or Glutamic acid.
<220> FEATURE:
<221> NAME/KEY: UNSURE
<222> LOCATION: (12)
<223> OTHER INFORMATION: The xaa at position 12 represents either
      Phenylalanine, Leucine, Methionine or Tyrosine.
<220> FEATURE:
<223> OTHER INFORMATION: Description of Artificial Sequence:  synthetic

<400> SEQUENCE: 119

Tyr Xaa Xaa Xaa Xaa Xaa Trp Trp Xaa Tyr Tyr Xaa
 1               5                  10

<210> SEQ ID NO 120
<211> LENGTH: 48
<212> TYPE: PRT
<213> ORGANISM: Artificial Sequence
<220> FEATURE:
<223> OTHER INFORMATION: Description of Artificial Sequence:  synthetic

<400> SEQUENCE: 120

Gly Gly Gly Ser Lys Val Ile Leu Phe Glu Gly Pro Ala Gly Arg Thr
 1               5                  10                  15

Ile Trp Glu Pro Lys Glu Ala Ser Asn His Thr Gly Ala Pro Gly Ser
            20                  25                  30

Lys Val Ile Leu Phe Glu Gly Gly Pro Gly His His His His His His
        35                  40                  45

<210> SEQ ID NO 121
<211> LENGTH: 44
<212> TYPE: PRT
<213> ORGANISM: Artificial Sequence
<220> FEATURE:
<223> OTHER INFORMATION: Description of Artificial Sequence:  synthetic

<400> SEQUENCE: 121

Gly Gly Gly Ser Lys Val Ile Leu Phe Glu Gly Pro Ala Gly Arg Trp
 1               5                  10                  15

Thr Trp Glu Pro Ile Ser Glu Gly Ala Pro Gly Ser Lys Val Ile Leu
            20                  25                  30

Phe Glu Gly Gly Pro Gly His His His His His His
        35                  40

<210> SEQ ID NO 122
<211> LENGTH: 44
<212> TYPE: PRT
<213> ORGANISM: Artificial Sequence
<220> FEATURE:
<223> OTHER INFORMATION: Description of Artificial Sequence:  synthetic

<400> SEQUENCE: 122

Gly Gly Gly Ser Lys Val Ile Leu Phe Glu Gly Pro Ala Gly Ser Gly
```

```
                        -continued
1               5              10             15
Ser Ala Gly Ser Gly Ala Ser Gly Ala Pro Gly Ser Lys Val Ile Leu
            20                  25                  30

Phe Glu Gly Gly Pro Gly His His His His His
        35                  40
```

FLUORESCENT DYE BINDING PEPTIDES

This application is a continuation of U.S. application Ser. No. 09/419,381, filed Oct. 15, 1999, now U.S. Pat. No. 6,747,135 which claims the benefit of U.S. provisional application Ser. No. 60/104,465, filed Oct. 16, 1998.

FIELD OF THE INVENTION

The invention relates to peptides that bind to fluorescent dyes, termed "fluorettes", and to methods of making and using the fluorettes. In particular, the fluorettes can be used in detection and assay systems in vitro and in vivo.

BACKGROUND OF THE INVENTION

Fluorophore dyes, due to their exquisite sensitivity and ease of use, are widely used in numerous approaches in fluorescent microscopy, flow cytometry and other detection systems (Haugland. Handbook of fluorescent probes and research chemicals (sixth edition). Molecular Probes, Inc., Eugene Oreg. (1996) and ref. therein).

Detection of proteins in living cells using fluorescence approaches has been accomplished in a variety of settings. For instance, it is possible to use ligands (or naturally-derived antibodies) conjugated directly or indirectly to fluorophores as probes of the expression levels of nearly any given surface-expressed protein on living cells. In some particular cases for proteins within cells, it is possible to use permeable ligands for individual target proteins. In these cases the ligand is either self-fluorescent, becomes fluorescent upon binding or is conjugated to fluorescent adducts. In other cases, it has been possible for many years to genetically fuse reporter enzymes such as β-galactosidase, β-glucuronidase, and β-glucosidase to proteins and use a fluorogenic dye, acted upon by the reporter enzyme(s), to assay enzymatic activity on a cell by cell basis (Nolan et al. Proc. Natl. Acad. Sci. U.S.A. 85:2603-2607 (1988); Lorincz et al. Cytometry 24:321-329 (1996); Krasnow et al. Science. 251:81-85 (1991). Other systems, including β-lactamase (Zlokarnik et al. Science 279:84-88(1998)) build upon those findings by applying dyes with increased cell permeability or having radiometric fluorescent qualities that might have advantages in some applications. In recent years proteins with inherent fluorescence, such as Green Fluorescent Protein (Welsh and Kay. Curr. Opin. Biotechnol. 8:617-622 (1997); Misteli and Spector. Nat. Biotechnol. 15:961-964 (1997)) have become widespread in their application owing to ease of use, the availability of mutant proteins with differing spectral qualities in either excitation or emission, and the relative non-toxicity of the approach.

However, in the aforementioned cases the approaches are limited by a need to genetically fuse a relatively bulky reporter protein to the molecule under study. This can have detrimental consequences to the functionality of the protein in question or interfere mechanistically with cellular constituents with which the protein interacts. While it would be best to directly measure a given target protein using a specific fluorescent dye that recognized any given target moiety, no technology exists as yet to create such reagents.

There is a need, therefore, to develop approaches that provide the building blocks for specific biomaterial detection.

SUMMARY OF THE INVENTION

The invention provides peptides that bind to fluorophore dyes. In one aspect of the invention the peptides are made of naturally occuring amino acids, non-naturally occurring amino acids, or combinations thereof.

In another aspect of the invention, methods are provided for isolating and identifying peptides that bind to fluorophore dyes. The method comprises creating and screening peptide libraries that bind to fluorophores.

In another aspect of the invention, methods are provided for increasing the binding affinity of the fluorette for a fluorophore.

In a further aspect of the invention are provided complexes of fluorettes bound to fluorophore dyes. The binding of the fluorophore by the fluorette may alter the excitation and/or the emission spectrum of the fluorophore.

In an additional aspect, the present invention provides methods for detecting a fluorette by binding a fluorette to a fluorophore dye and detecting the fluorette/fluorophore dye complex.

DETAILED DESCRIPTION OF THE INVENTION

Figure 1:
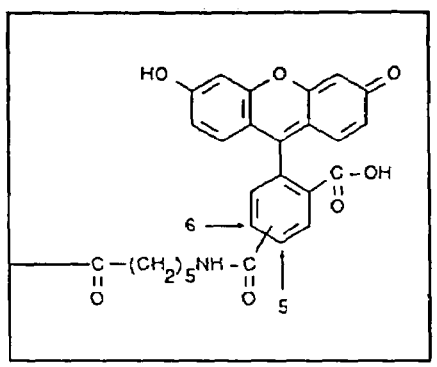
FIG. 1. Fluorophore dye carriers. Fluorescein, Oregon Green 514, Rhodamine Red and Texas Red activated derivatives were covalently linked to the polymer carrier Ultralink Immobilized DADPA via a 12-atom diaminodipropylamine spacer. A spacer is shown as a horizontal thick bar. Digits with arrows in the chemical structures of all fluorophore dyes, except Oregon Green 514, show that "mixed isomers" of these fluorophore dye activated derivatives were used for a coupling.
Figure 1:
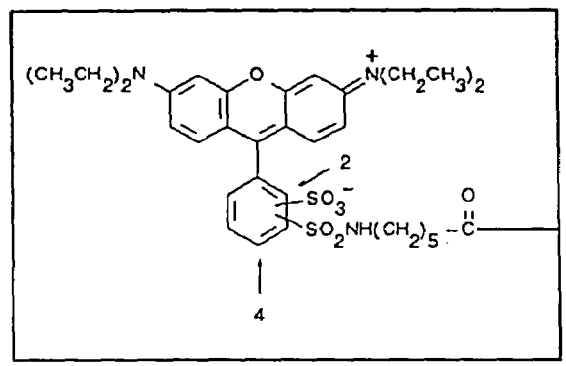
Figure 1:
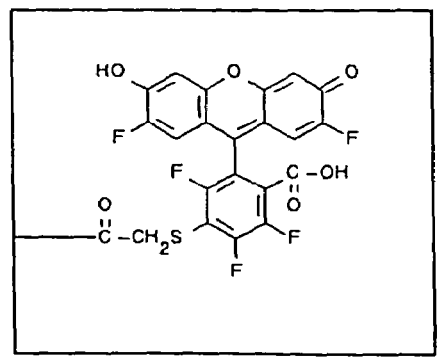
Figure 1:
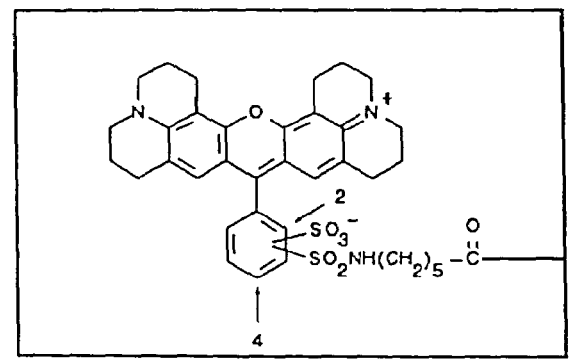

The present invention provides novel peptides or "fluorettes" that specifically bind fluorophore dyes. The present invention also provides novel compositions comprising multimeric fluorettes and fluorettes fused or linked to other compounds or molecules. Also provided are methods to create and modify fluorettes.

The present invention further provides methods for the use of fluorettes in detecting biological materials, molecules, or target analytes, intracellular events, and intermolecular and intramolecular interactions. The fluorettes also find use in in vitro assays and high throughput screens. The methods provided are based on the formation and detection of a fluorette/fluorophore dye complex.

The compositions and methods of the present invention provide a significant improvement over conventional light-emitting techniques. Fluorettes, due to their small size, are not intrusive to the systems being studied and, therefore, permit detection and analysis of a target moiety or molecule while minimizing target modification. Current light-emitting detection methods involve the use of enzyme-generated fluorochromes, luciferase-generated light, or reporter systems using engineered, inherently fluorescent proteins such as *Aequoria victoria* green fluorescent protein (GFP). These systems are unwieldy and bulky and are intrusive to the system being studied; often necessitating the synthesis of large fusion proteins or out of context genomic constructions. Thus, conventional techniques can involve substantial genetic manipulations of the targets one is trying to study, which may disrupt, interfere, or alter the process being measured. Fluorettes minimize or avoid these limitations.

Accordingly, the present invention provides a peptide, sometimes termed a "fluorette" herein, that will bind a fluorescent dye.

By "peptide" or "fluorette" herein is meant at least about 8 covalently attached amino acids. The peptide may be made up of naturally occurring amino acids and peptide bonds, or synthetic peptidomimetic structures. Thus "amino acid", or "peptide residue", as used herein means both naturally occurring and synthetic amino acids. For example, homophenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. The peptides can be linear or branched. Amino acids includes naturally occurring amino acids or non-naturally occurring amino acids.

By "naturally-occurring amino acids" herein is meant amino acids that are produced by living organisms. Naturally-occurring amino acids are preferred in in vivo embodiments.

By "non-naturally-occurring amino acids" herein is meant amino acids not produced by a living organism but that can be chemically synthesized. Non-naturally-occurring amino acids include, for example, stereoisomers or enantiomers of the naturally-occurring amino acids in which the amino side chains, are in either the (D)((R)) or (S)((L)) configuration; amino acids in which an amine group is bonded to any other but the alpha-carbon or may have more than one amine group bonded to the alpha-carbon; and amino acids having functional groups or "R" groups not known to occur in nature.

The length of the peptide or fluorette, i.e., the number of amino acids, will vary. In general, the number of amino acids varies from about 8 to about 50, with from about 8 to about 40 being preferred, from about 8 to about 25 being particularly preferred, and from about 8 to about 12 being especially preferred. Thus, "peptide" includes peptides, oligopeptides, and in some cases, proteins.

The fluorette can be monomeric or multimeric. That is, a monomeric fluorette binds a single fluorophore. A multimeric fluorette is two or more associated monomeric fluorettes. The association of a multimeric fluorette can be either covalent or non-covalent. For example, the monomers can be joined directly together, for example as a linear fusion (i.e., the carboxy terminus of one is joined to the amino terminus of the second), or as a branched fusion, wherein the attachment of the second monomer is other than to the backbone of the first. In addition, a chemical cross-linker or inclusion of specific reactive group on a fluorette be used to join fluorette monomers. Alternatively the monomers may be non-covalently associated; for example, as is more fully outlined below, dimerization sequences can be used to associate two monomers.

A multimeric fluorette can be homomultimeric, i.e., all the monomers are the same, and bind the same fluorophore dye, or heteromultimeric, having at least two different fluorette monomers and can bind different fluorophores.

The fluorette peptides bind to at least one fluorophore dye.

By "binding" herein generally is meant a non-covalent association or interaction between a fluorette and a fluorescent dye. The non-covalent interactions between the fluorette and dye may involve various types of electrostatic, hydrophilic, and hydrophobic interactions. Binding may also involve forming one or more covalent bonds between the fluorette and the dye. Covalent bonds can be formed directly between the fluorette and the dye or can be formed by a cross linker or by inclusion of a specific reactive group on either the fluorette or dye or both molecules. Binding may also involve a combination of covalent and non-covalent interactions.

In a preferred embodiment, the binding is specific. By "specific binding" herein is meant that the fluorophores will preferentially bind to a fluorophore dye with a binding constant in the range of at least about $10^{-6}$ $M^{-1}$ to about $10^{-10}$ $M^{-1}$, with a preferred range being from at least about $10^{-6}$ $M^{-1}$ to about $10^{-7}$ $M^{-1}$, with an especially preferred range of from at least about $10^{-7}$ $M^{-1}$ to about $10^{-10}$ $M^{-1}$. In a preferred embodiment, the fluorettes do not specifically bind to other fluorophore dyes or compounds or moieties; that is, a fluorette is specific to one fluorophore. Alternatively, a fluorette may bind two or more fluorescent dyes (bind together 2 or more fluorophores or more or capable of binding independently two or more fluorophores); that is, a fluorette may specifically bind another compound or moiety, including another fluorophore, if these molecules have a common structural feature(s) that specifically interact with the fluorette. Preferably, however, a fluorette will not appreciably bind compounds other than fluorescent dyes.

In other embodiments, a dye is non-fluorescent but becomes fluorescent when bound by a fluorette. In further embodiments, fluorette binding to a non-fluorescent dye causes the release of a fluorescent moiety. When the fluorescent moiety is released, the fluorette may bind to the released fluorescent moiety, may bind to the non-fluorescent dye, or may be released and therefore free to bind a second molecule of the non-fluorescent dye and repeat this process.

By "fluorescent dye" or "fluorophore" or "fluorophore dye" herein is meant a compound that absorbs an incident light of a characteristic range of wavelengths or excitation spectrum and dissipates the absorbed energy by emitting light of a characteristic range of wavelengths or emission spectrum. By "excitation spectrum" herein is meant the wavelength of incident light absorbed by the fluorophore dye that causes the fluorophore dye to fluoresce. By "emission spectrum" herein is meant the characteristic wavelengths of the emitted or fluorescent light produced as the energy of the absorbed incident light is released. The excitation and emission spectra for a fluorophore dye may or may not overlap. In a preferred embodiment the incident light is in the ultraviolet spectrum and the emitted light is in the visible spectrum.

Preferred fluorophores include, but are not limited to, Texas Red, Rhodamine Red, Oregon Green 514, and Fluorescein. Examples of fluorescent dyes are found in the Molecular Probes Catalog, 6th Ed., Richard Haugland, Ed., which is expressly incorporated by reference in its entirety.

In addition, the fluorette can further comprise additional components, such as a fusion partner or functional group. By "fusion partner" or "functional group" herein is meant a sequence that is associated with the fluorettes, that confers upon the fluorette a function or ability. Fusion partners can be heterologous (i.e. not native to a host cell), or synthetic (not native to any cell). Suitable fusion partners include, but are not limited to: a) presentation structures, as defined below, which provide the fluorettes in a conformationally restricted or stable form; b) targeting sequences, defined below, which allow the localization of the flourette into a subcellular or extracellular compartment; c) rescue sequences as defined below, which allows the purification or isolation of the fluorette; d) stability sequences, which confer stability or protection from degradation to the fluorette, for example resistance to proteolytic degradation; e) dimerization sequences, to allow for fluorette dimerization or multimerization; or f) any combination of a), b), c), d), and e), as well as linker sequences as needed.

In a preferred embodiment, the fusion partner is a presentation structure. By "presentation structure" or grammatical equivalents herein is meant a sequence, which, when fused to the fluorette, causes the fluorette to assume a conformationally restricted form. Proteins interact with other proteins and molecules largely through conformationally constrained domains. Although small peptides with freely rotating amino- and carboxy-termini can have potent functions as is known in the art, the conversion of such peptide structures into active agents can be difficult due to the inability to predict side-chain positions for peptidomimetic synthesis. Therefore the presentation of fluorettes in conformationally constrained structures will likely lead to higher affinity interactions of the fluorette with its target fluorophore dye. This fact has been recognized in the combinatorial library generation systems using biologically generated short peptides in bacterial phage systems. A number of workers have constructed small domain molecules in which one might present biased-combinatorial libraries of peptide structures.

While the fluorettes are peptides, presentation structures are preferably peptides or proteins. Thus, synthetic presentation structures, i.e. artificial polypeptides, are capable of presenting fluorettes as a conformationally-restricted domain. Generally such presentation structures comprise a first portion joined to the N-terminal end of the flourette, and a second portion joined to the C-terminal end of the flourette; that is, the flourette is inserted into the presentation structure, although variations may be made, as outlined below. To increase the affinity or specificity of the fluorette, the presentation structures are selected or designed to have minimal biologically activity when expressed in the target cell.

Preferred presentation structures maximize accessibility to the flourette by presenting it on an exterior loop. Accordingly, suitable presentation structures include, but are not limited to, minibody structures, loops on beta-sheet turns and coiled-coil stem structures in which residues not critical to structure are randomized, zinc-finger domains, cysteine-linked (disulfide) structures, transglutaminase linked structures, cyclic peptides, B-loop structures, helical barrels or bundles, leucine zipper motifs, etc. In addition, presentation structures include dimerization sequences, as defined below.

In a preferred embodiment, the presentation structure is a coiled-coil structure, allowing the presentation of the flourette on an exterior loop. (See, for example, Myszka et al., Biochem. 33:2362-2373 (1994), hereby incorporated by reference). Using this system investigators have isolated peptides capable of high affinity interaction with the appropriate target. In general, coiled-coil structures allow for between 6 to 20 amino acids.

A preferred coiled-coil presentation structure is as follows: MGC<u>AALESEVSALESEVAS</u>LESEVAALX$_{(n)}$ <u>LAAVKSKLSAVKSKLASVKSKLAA</u>CGPP (SEQ ID NO:49). The underlined regions represent a coiled-coil leucine zipper region defined previously (see Martin et al., EMBO J. 13(22):5303-5309 (1994), incorporated by reference). The bolded X$_{(n)}$ region represents the loop structure and when appropriately replaced with peptides (i.e. fluorettes, generally depicted herein as (X)$_n$, where X is an amino acid residue and n is an integer of at least 5 or 6) can be of variable length. The replacement of the bolded region is facilitated by encoding restriction endonuclease sites in the underlined regions, which allows the direct incorporation of oligonucleotides at these positions. For example, a preferred embodiment generates an XhoI site at the double underlined LE site and a HindIII site at the double-underlined KL site.

In a preferred embodiment, the presentation structure is a minibody structure. A "minibody" is essentially composed of a minimal antibody complementarity region. The minibody presentation structure generally provides two randomizing regions that in the folded protein are presented along a single face of the tertiary structure. (See for example Bianchi et al., J. Mol. Biol. 236(2):649-59 (1994), and references cited therein, all of which are incorporated by reference). Investigators have shown this minimal domain is stable in solution and have used phage selection systems in combinatorial libraries to select minibodies with peptide regions exhibiting high affinity, Kd=$10^{-7}$, for the pro-inflammatory cytokine IL-6.

A preferred minibody presentation structure is as follows: MGRNSQATSGFTFSHFYMEWVRGGEYIMSR HKHNKYTTEYSASVKGRYIVSRDTSQSILYLQKKKG-PP (SEQ ID NO:50). The bold, underline regions are the regions which may be contain fluorette sequences. The italicized phenylalanine must be invariant in the first randomizing region. The entire peptide is cloned in a three-oligonucleotide variation of the coiled-coil embodiment, thus allowing two different randomizing regions to be incorporated simultaneously. This embodiment utilizes non-palindromic BstXI sites on the termini.

In a preferred embodiment, the presentation structure is a sequence that contains generally two cysteine residues, such that a disulfide bond may be formed, resulting in a conformationally constrained sequence. This embodiment is particularly preferred when fluorettes are to be secreted from a cell. As will be appreciated by those in the art, any number of flourettes, with or without spacer or linking sequences, may be flanked with cysteine residues. In other embodiments, effective presentation structures may be generated by the flourettes themselves. For example, the flourettes may be "doped" with cysteine residues which, under the appropriate redox conditions, may result in highly crosslinked structured conformations, similar to a presentation structure. Similarly, the flourettes may be controlled to contain a certain number of residues to confer β-sheet or α-helical structures.

In a preferred embodiment, a presentation structure is neuropeptide head activator. Bodenmuller et al. EMBO J. 5(8), 1825-1829 (1983) showed that neuropeptide head activator (HAv) dimerized to yield a biologically inactive form of the peptide at concentration as low as $10^{-13}$M, thus indicating extremely high self-binding affinity. Aldwin et al. U.S. Pat. No. 5,491,074 observed that a fragment containing the last six amino acids of this peptide's carboxyl terminus (SKVILF) (SEQ ID NO:51) resulted in dimers that were even more stable than the HA itself. The U.S. Pat. No. 5,491,074 shows that the last amino acid of SKVILF, the F (phenylalanine), must be on the carboxyl terminus for a proper peptide dimerization activity. However, if F is not on the carboxyl terminus, it must be followed by one of two amino acids with free carboxyl group, E or D, to maintain the peptide dimerization. Therefore, if the dimerizing peptide positioned inside a carrier protein, 6-mer SKVILF sequence must be converted to 7-mer SKVILFE (SEQ ID NO:51) or SKVILFD (SEQ ID NO:53) sequences. For example, a presentation structure comprising neuropeptide head activator peptides comprises: SKVILFE/D(X) $_n$SKVILFE/D (SEQ ID NO:112); wherein X represents any amino acid, and n is at least about 8 amino acids. Linkers or spacers as known in the art are optionally placed between the HAv peptides and the variable ((X)$_n$) region and optionally placed at the amino and carboxy terminus of the structure.

Positioning of peptides of between two SKVILFE(D) sequences makes the peptides constrained. Upon SKVILFE (D)-SKVILFE(D) intramolecular interaction, the peptide structure is converted from linear to a loop or mini-domain such that the peptide becomes structurally constrained. This provides three important advantages. First, peptides in constrained conformations usually have higher affinity for a ligand than the same peptide in linear conformation. Second, the constrained peptide has a higher protease resistance than the linear peptide as a result of the formation of a "rigid surface" structure. Third, and more importantly, transfer of a constrained peptide as a cassette to a protein carrier will not dramatically change its original conformation (and consequently its binding activity) while a linear peptide is more likely to show a decrease in binding activity.

In a preferred embodiment, the fusion partner is a targeting sequence. As will be appreciated by those in the art, the localization of proteins within a cell is a simple method for increasing effective concentration. The localization of a peptide to a specific cellular location, such as a membrane, limits its search for its ligand to that limited dimensional space. Alternatively, the concentration of a protein or polypeptide can also be simply increased by nature of the localization. For example, shuttling the fluorettes into the nucleus confines them to a smaller space thereby increasing the concentration. Finally, the ligand or target may simply be localized to a specific compartment. As will be appreciated by those in the art, when a fluorette is fused to another protein, as outlined herein, the targeting sequence can be fused to the protein partner as well.

Thus, suitable targeting sequences include, but are not limited to, binding sequences capable of causing binding of the fluorette to a predetermined molecule or class of molecules while retaining activity of the fluorette, (for example by using enzyme inhibitor or substrate sequences to target a class of relevant enzymes); sequences signalling selective degradation, of itself or co-bound proteins; and signal sequences capable of constitutively localizing the fluorette to a predetermined cellular locale, including a) subcellular locations such as the Golgi, endoplasmic reticulum, nucleus, nucleoli, nuclear membrane, mitochondria, chloroplast, secretory vesicles, lysosome, and cellular membrane; and b) extracellular locations via a secretory signal. Particularly preferred is localization to either subcellular locations or to the outside of the cell via secretion.

In a preferred embodiment, the targeting sequence is a nuclear localization signal (NLS). NLSs are generally short, positively charged (basic) domains that serve to direct the entire protein in which they occur to the cell's nucleus. Numerous NLS amino acid sequences have been reported including single basic NLS's such as that of the SV40 (monkey virus) large T Antigen (Pro Lys Lys Lys Arg Lys Val) (SEQ ID NO:54), Kalderon (1984), et al., Cell, 39:499-509; the human retinoic acid receptor-β nuclear localization signal (ARRRRP) (SEQ ID NO:55); NFkB p50 (EEVQRKRQKL SEQ ID NO:56); Ghosh et al., Cell 62:1019 (1990); NFkB p65 (EEKRKRTYE (SEQ ID NO:57); Nolan et al., Cell 64:961 (1991); and others (see for example Boulikas, J. Cell. Biochem. 55(1):32-58 (1994), hereby incorporated by reference) and double basic NLS's exemplified by that of the Xenopus (African clawed toad) protein, nucleoplasmin (Ala Val Lys Arg Pro Ala Ala Thr Lys Lys Ala Gly Gln Ala Lys Lys Lys Lys Leu Asp) (SEQ ID NO:58), Dingwall, et al., Cell, 30:449-458, 1982 and Dingwall, et al., J. Cell Biol., 107:641-849; 1988). Numerous localization studies have demonstrated that NLSs incorporated into peptides or grafted onto proteins not normally targeted to the cell nucleus cause these peptides and proteins to be concentrated in the nucleus. See, for example, Dingwall, and Laskey, Ann, Rev. Cell Biol., 2:367-390, 1986; Bonnerot, et al., Proc. Natl. Acad. Sci. USA, 84:6795-6799, 1987; Galileo, et al., Proc. Natl. Acad. Sci. USA, 87:458-462, 1990.

In a preferred embodiment, the targeting sequence is a membrane anchoring signal sequence. This is particularly useful since many parasites and pathogens bind to the membrane, in addition to the fact that many intracellular events originate at the plasma membrane. Thus, membrane-bound fluorettes are useful for both the identification of important elements in these processes as well as for the discovery of effective inhibitors. The invention provides methods for presenting the fluorettes extracellularly or in the cytoplasmic space. For extracellular presentation, a membrane anchoring region is provided at the carboxyl terminus of the peptide presentation structure. In another embodiment, for extracellular presentation, a membrane anchoring region is provided at the amino terminus of the peptide presentation structure. Preferably, the amino terminal anchoring region functions as the anchoring region of a Type 2 glycoprotein. The fluorette is expressed on the cell surface and presented to the extracellular space, such that it can bind its target fluorophore. The binding of a fluorette, espescially when fused to a polypeptide or protein could confer a function on the cells expressing the fluorette. The cytoplasmic region could be neutral or could contain a domain that, when the fluorette is bound, confers a function on the cells (activation of a kinase, phosphatase, binding of other cellular components to effect function). Similarly, the fluorette could be contained within a cytoplasmic region, and the transmembrane region and extracellular region remain constant or have a defined function.

Membrane-anchoring sequences are well known in the art and are based on the geometry of mammalian transmembrane molecules. Peptides are inserted into the membrane based on a signal sequence (designated herein as ssTM) and require a hydrophobic transmembrane domain (herein TM). The transmembrane proteins are inserted into the membrane such that the regions encoded 5' of the transmembrane domain are extracellular and the sequences 3' become intracellular. Of course, if these transmembrane domains are placed 5' of the variable region, they will serve to anchor it as an intracellular domain, which may be desirable in some embodiments. ssTMs and TMs are known for a wide variety of membrane bound proteins, and these sequences may be used accordingly, either as pairs from a particular protein or with each component being taken from a different protein, or alternatively, the sequences may be synthetic, and derived entirely from consensus as artificial delivery domains.

As will be appreciated by those in the art, membrane-anchoring sequences, including both ssTM and TM, are known for a wide variety of proteins and any of these may be used. Particularly preferred membrane-anchoring sequences include, but are not limited to, those derived from CD8, ICAM-2, IL-8R, CD4 and LFA-1.

Useful sequences include sequences from: 1) class I integral membrane proteins such as IL-2 receptor beta-chain (residues 1-26 are the signal sequence, 241-265 are the transmembrane residues; see Hatakeyama et al., Science 244:551 (1989) and von Heijne et al, Eur. J. Biochem. 174:671 (1988)) and insulin receptor beta chain (residues 1-27 are the signal, 957-959 are the transmembrane domain and 960-1382 are the cytoplasmic domain; see Hatakeyama, supra, and Ebina et al., Cell 40:747 (1985)); 2) class II integral membrane proteins such as neutral endopeptidase (residues 29-51 are the transmembrane domain, 2-28 are the cytoplasmic domain; see Malfroy et al., Biochem. Biophys. Res. Commun. 144:59 (1987)); 3) type III proteins such as human cytochrome P450 NF25 (Hatakeyama, supra); and 4) type IV proteins such as human P-glycoprotein (Hatakeyama, supra). Particularly preferred are CD8 and ICAM-2. For example, the signal sequences from CD8 and ICAM-2 lie at the extreme 5' end of the transcript. These consist of the amino acids 1-32 in the case of CD8 (MASPLTRFLSLNLLLLGESILGSGEAKPQAP; (SEQ ID NO:59) Nakauchi et al., PNAS USA 82:5126 (1985) and 1-21 in the case of ICAM-2 (MSSFGYRTLTVALFTLIC-CPG (SEQ ID NO:60); Staunton et al., Nature (London) 339:61 (1989)). These leader sequences deliver the fluorette to the membrane while the hydrophobic transmembrane domains, placed 3' of the fluorette region, serve to anchor the construct in the membrane. These transmembrane domains are encompassed by amino acids 145-195 from CD8 (PQRPEDCRPRGSVKGTGLDFACDIYIWA-PLAGICVALLLSLIITLICYHSR (SEQ ID NO:61); Nakauchi, supra) and 224-256 from ICAM-2 (MVIIVTVVSV-LLSLFVTSVLLCFIFGQHLRQQR (SEQ ID NO:62); Staunton, supra).

Alternatively, membrane anchoring sequences include the GPI anchor, which results in a covalent bond between the molecule and the lipid bilayer via a glycosyl-phosphatidylinositol bond for example in DAF (PNKGSGTTSGTTR-LLSGHTCFTLTGLLGTLVTMGLLT (SEQ ID NO:63), with the bolded serine the site of the anchor; see Homans et al., Nature 333(6170):269-72 (1988), and Moran et al., J. Biol. Chem: 266:1250 (1991)). In order to do this, the GPI sequence from Thy-1 can be cassetted 3' of the fluorette in place of a transmembrane sequence.

Similarly, myristylation sequences can serve as membrane anchoring sequences. It is known that the myristylation of c-src recruits it to the plasma membrane. This is a simple and effective method of membrane localization, given that the first 14 amino acids of the protein are solely responsible for this function: MGSSKSKPKDPSQR (SEQ ID NO:64) (see Cross et al., Mol. Cell. Biol. 4(9):1834 (1984); Spencer et al., Science 262:1019-1024 (1993), both of which are hereby incorporated by reference). This motif has already been shown to be effective in the localization of reporter genes and can be used to anchor the zeta chain of the TCR. This motif is placed 5' of the fluorette in order to localize it to the plasma membrane. Other modifications such as palmitoylation can be used to anchor fluorettes in the plasma membrane; for example, palmitoylation sequences from the G protein-coupled receptor kinase GRK6 sequence (LLQRLFSRQDCCGNCSDSEEELPTRL (SEQ ID NO:65), with the bold cysteines being palmitolyated; Stoffel et al., J. Biol. Chem 269:27791 (1994)); from rhodopsin (KQFRNCMLTSLCCGKNPLGD (SEQ ID NO:66); Barnstable et al., J. Mol. Neurosci. 5(3):207 (1994)); and the p21 H-ras 1 protein (LNPPDESGPGCMSCKCVLS (SEQ ID NO:67); Capon et al., Nature 302:33 (1983)).

In a preferred embodiment, the targeting sequence is a lysozomal targeting sequence, including, for example, a lysosomal degradation sequence such as Lamp-2 (KFERQ (SEQ ID NO:68); Dice, Ann. N.Y. Acad. Sci. 674:58 (1992); or lysosomal membrane sequences from Lamp-1 (MLIP-IAGFFALAGLVLIVLIAYLIGRKRSHAGYQTI (SEQ ID NO:69), Uthayakumar et al., Cell. Mol. Biol. Res. 41:405 (1995)) or Lamp-2 (LVPIAVGAALAGVLILVLLAYFIG LKHHHAGYEQF (SEQ ID NO:70), Konecki et la., Biochem. Biophys. Res. Comm. 205:1-5 (1994), both of which show the transmembrane domains in italics and the cytoplasmic targeting signal underlined).

Alternatively, the targeting sequence may be a mitrochondrial localization sequence, including mitochondrial matrix sequences (e.g. yeast alcohol dehydrogenase III; MLRTSS-LFTRRVQPSLFSRNILRLQST (SEQ ID NO:71); Schatz, Eur. J. Biochem. 165:1-6 (1987)); mitochondrial inner membrane sequences (yeast cytochrome c oxidase subunit IV; MLSLRQSIRFFKPATRTLCSSRYLL (SEQ ID NO:72); Schatz, supra); mitochondrial intermembrane space sequences (yeast cytochrome c1; MFSMLSKRWAQRTL-SKSFYSTATGAASKS-GKLTQKLVTAGVAAAGITASTLLYADSLTAEAMTA (SEQ ID NO:73); Schatz, supra) or mitochondrial outer membrane sequences (yeast 70 kD outer membrane protein; MKSFITRNKTAILATVMTG-TAIGAYYYYNQLQQQQQRGKK (SEQ ID NO:74); Schatz, supra).

The target sequences may also be endoplasmic reticulum sequences, including the sequences from calreticulin (KDEL; Pelham, Royal Society London Transactions B; 1-10 (1992)) or adenovirus E3/19K protein (LYLSRRS-FIDEKKMP (SEQ ID NO:75); Jackson et al., EMBO J. 9:3153 (1990)).

Furthermore, targeting sequences also include peroxisome sequences (for example, the peroxisome matrix sequence from Luciferase; SKL; Keller et al., PNAS USA 4:3264 (1987)); farnesylation sequences (for example, P21 H-ras 1; LNPPDESGPGCMSCKCVLS (SEQ ID NO:76), with the bold cysteine farnesylated; Capon, supra); geranylgeranylation sequences (for example, protein rab-5A; LTEPTQPTRNQCCSN (SEQ ID NO:77), with the bold cysteines geranylgeranylated; Farnsworth, PNAS USA 91:11963 (1994)); or destruction sequences (cyclin B1; RTALGDIGN (SEQ ID NO:78); Klotzbucher et al., EMBO J. 1:3053 (1996)).

In a preferred embodiment, the targeting sequence is a secretory signal sequence capable of effecting the secretion of the fluorette. There are a large number of known secretory signal sequences which are placed 5' to the fluorette sequence and are cleaved from the peptide region to effect secretion into the extracellular space. Secretory signal sequences and their transferability to unrelated proteins are well known, e.g., Silhavy, et al. (1985) Microbiol. Rev. 49, 398-418. This is particularly useful to generate a fluorette that is expressed at the surface of a cell. In a preferred approach, a fusion product is configured to contain, in series, secretion signal peptide-presentation structure-flourette-presentation structure. In this manner, target cells grown in the vicinity of cells caused to express the fluorettes, are bathed in secreted fluorette. Target cells exhibiting a phenotypic change in response to the presence of a fluorette, or internalization of the fluorette and binding to intracellular targets, are localized by any of a variety of methods, such as, FRET analysis (Selvin et al. Methods Enzymol. 246:300-334 (1995)) as described below.

Suitable secretory sequences are known, including signals from IL-2 (MYRMQLLSCIALSLALVTNS (SEQ ID NO:79); Villinger et al., J. Immunol. 155:3946 (1995)), growth hormone (MATGSRTSLLLAFGLLCLP-WLQEGSAFPT (SEQ ID NO:80); Roskam et al., Nucleic Acids Res. 7:30 (1979)); preproinsulin (MALWMRLL-PLLALLALWGPDPAAAFVN (SEQ ID NO:81); Bell et al., Nature 284:26 (1980)); and influenza HA protein (MKAK-LLVLLYAFVAGDQI (SEQ ID NO:82); Sekiwawa et al., PNAS 80:3563)), with cleavage between the non-underlined-underlined junction. A particularly preferred secretory signal sequence is the signal leader sequence from the secreted cytokine IL4, which comprises the first 24 amino acids of IL-4 as follows: MGLTSQLLPPLFFLLACAGN-FVHG (SEQ ID NO:83).

In a preferred embodiment, the fusion partner is a rescue sequence. A rescue sequence is a sequence which may be used to purify or isolate the fluorette (or, in some cases, the nucleic acid encoding it). Thus, for example, peptide rescue sequences include purification sequences such as the His$_6$ tag for use with Ni affinity columns and epitope tags for detection, immunoprecipitation or FACS (fluorescence-activated cell sorting). Suitable epitope tags include myc (for use with the commercially available 9E10 antibody), the BSP biotinylation target sequence of the bacterial enzyme BirA, flu tags, lacZ, and GST.

In a preferred embodiment, a fluorette sequence functions as a rescue sequence. The fluorette because it binds a fluorophore dye can be used to purify or isolate a molecule to which it is fused or attached by affinity chromatography using fluorophore dye columns. If the fluorette alters the excitation or emission spectrum of the bound fluorophore dye, as described below, this difference can be used to monitor attachment and/or elution of the fluorette from the affinity column. Alternatively, the fluorette/dye complex can be used in FACS. If desired, a linker joining the fluorette to its fusion partner also contains a convenient site or sites to seperate the fluorette from the fusion partner, such as, a unique protease recognition sequences. Alternatively, the affinity column can contain antibody reactive with the fluorette.

In a preferred embodiment, the fusion partner is a stability sequence to confer stability to the fluorette. Thus, for example, fluorettes may be stabilized by the incorporation of glycines after an amino-terminal methionine (MG or MGG0), for protection of the fluorette to ubiquitination as per Varshavsky's N-End Rule, thus conferring long half-life in the cytoplasm. Similarly, two prolines at the C-terminus impart upon peptides resistance to carboxypeptidase action. The presence of two glycines prior to the prolines impart both flexibility and prevent structure initiating events in the di-proline to be propagated into the fluorette structure. Thus, preferred stability sequences are as follows: MG(X)$_n$GGPP (SEQ ID NO:84), where (X)$_n$ is a fluorette of any amino acid and n is an integer of at least about 8, as outlined above for fluorette length.

In a preferred embodiment, the fusion partner is a dimerization sequence. A dimerization sequence allows the non-covalent association of one fluorette to another fluorette, with sufficient affinity to remain associated under normal physiological conditions. The dimers may be homo- or heterodimers.

Dimerization sequences may be a single sequence that self-aggregates, or two sequences. That is, a first fluorette with dimerization sequence 1, and a second fluorette with dimerization sequence 2, such that upon introduction into a cell and expression of the nucleic acids, dimerization sequence 1 associates with dimerization sequence 2 to form new random peptide structures. In addition, dimerization sequences can be used as presentation structures. That is, by putting a first dimerization sequence at one terminus of the fluorette, and a second dimerization sequence at the other terminus, similar to some other presentation structures, a "cyclized" fluorette can be made.

Suitable dimerization sequences will encompass a wide variety of sequences. Any number of protein-protein interaction sites are known. In addition, dimerization sequences may also be elucidated using standard methods such as the yeast two hybrid system, and traditional biochemical affinity binding studies, or even using the present methods.

The fusion partners may be placed anywhere (i.e. N-terminal, C-terminal, internal) in the structure as the biology and activity permits, although in general, N- or C-terminal fusions are preferred to fusions internal to the fluorette sequence.

In another embodiment, a fluorette occupies an internal position within the fusion partner as the biology and activity permits. This will allow a means to measure access of the fluorette for its fluorophore dye as a means of determining structure and function of the region in which the fluorette resides.

In a preferred embodiment, the fusion partner includes a linker or tethering sequence. Linker sequences between various targeting sequences (for example, membrane targeting sequences) and the other components of the constructs and fluorettes may be desirable to allow the candidate agents to interact with potential targets unhindered. For example, useful linkers include glycine-serine polymers (including, for example, $(GS)_n$ (SEQ ID NO:85), $(GSGGS)_n$ (SEQ ID NO:86) and $(GGGS)_n$ (SEQ ID NO:87), where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies. As is more fully outlined below, linkers such as these may also be used in some embodiments between fluorettes and the moiety to which they are fused.

In alternative embodiments linkers can also be sequences that are derived from other proteins and have no structure or an assumed structure. In another embodiment the linkers distance the fluorette from a molecule to which they are attached, for example, a fusion protein.

In addition, the fusion partners, including presentation structures, may be modified, randomized, and/or matured to alter the presentation orientation of the fluorette. For example, determinants at the base of the loop may be modified to slightly modify the internal loop tertiary structure, which maintains the fluorette amino acid sequence.

In a preferred embodiment, combinations of fusion partners are used. Thus, for example, any number of combinations of presentation structures, targeting sequences, rescue sequences, and stability sequences may be used, with or without linker sequences.

In a preferred embodiment, the fluorette is fused to a target analyte, for example, to monitor or follow the target analyte, as is more fully described below. By "target analyte" or "analyte" or grammatical equivalents herein is meant any molecule, compound or particle to be detected. As will be appreciated by those in the art, a large number of analytes may be detected using the present methods; basically, any target analyte to which a fluorette may be attached may be detected using the methods of the invention.

Suitable analytes include organic and inorganic molecules, including biomolecules. In a preferred embodiment, the analyte may be an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are proteins.

In a preferred embodiment, the target analyte is a protein and the fluorette is made as a fusion protein, using techniques well known in the art. For example, the nucleic acid encoding the fluorette is linked in-frame with a nucleic acid encoding a target protein to produce a fusion nucleic acid. Preferably, fusion proteins are produced by culturing a host cell transformed with an expression vector containing the fusion nucleic acid, under the appropriate conditions to induce or cause expression of the fusion protein. The conditions appropriate for fusion protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of expression is important.

Alternatively, fluorettes can be produced by in vitro transcription of the encoding nucleic acid and translation of the RNA transcript, as known in the art.

In a preferred embodiment, the target analyte is other than a protein, and the fusion of the fluorette to the target analyte is generally done chemically. In general, the fluorette and the target analyte are attached through the use of functional groups on each that can then be used for attachment. Preferred functional groups for attachment are amino groups, carboxy groups, oxo groups and thiol groups. These functional groups can then be attached, either directly or indirectly through the use of a linker. Linkers are well known in the art; for example, homo-or hetero-bifunctional linkers as are well known (see 1994 Pierce Chemical Company catalog, technical section on cross-linkers, pages 155-200, incorporated herein by reference). In an additional embodiment, carboxyl groups (either from the surface or from the candidate agent) may be derivatized using well known linkers (see the Pierce catalog). For example, carbodiimides activate carboxyl groups for attack by good nucleophiles such as amines (see Torchilin et al., Critical Rev.

Therapeutic Drug Carrier Systems, 7(4):275-308 (1991), expressly incorporated herein). Proteinaceous species may also be attached using other techniques known in the art, for example for the attachment of antibodies to polymers; see Slinkin et al., Bioconj. Chem. 2:342-348 (1991); Torchilin et al., supra; Trubetskoy et al., Bioconj. Chem. 3:323-327 (1992); King et al., Cancer Res. 54:6176-6185 (1994); and Wilbur et al., Bioconjugate Chem. 5:220-235 (1994), all of which are hereby expressly incorporated by reference). It should be understood that the fluorettes and target analytes may be attached in a variety of ways, including those listed above. What is important is that manner of attachment does not significantly alter the functionality of the fluorette (and preferably the target analyte as well); that is, the attachment should be done in such a flexible manner as to allow the interaction of the fluorette peptide with a dye, and the target analyte to its binding partners.

In a preferred embodiment the fluorette will bind to Texas Red. Suitable fluorettes in this embodiment include, but are not limited to, KHVQYWTQMFYS (SEQ ID NO:1); DFLQWKLARQKP (SEQ ID NO:2); KPVQYWTQMFYT (SEQ ID NO:15); KPAQYVVTQMFYS (SEQ ID NO:16); KNVQYWVTQMFYT (SEQ ID NO:17); KHVQYV(TH-MFYT (SEQ ID NO:18); KHVQYWTQMFYT (SEQ ID NO:19); NHVHYWTQMFYS (SEQ ID NO:20); THVQYV-VTQMFYS (SEQ ID NO:21); RTIWEPKEASNHT (SEQ ID NO:105): WSKMGHTVT (SEQ ID NO:106); RWTWEPISE (SEQ ID NO:107); GNQKCLQHNRCST (SEQ ID NO:108); SQTWSFPEH (SEQ ID NO:109); EPMARPWERKQDR (SEQ ID NO:110); and GTLSA-TRPYGRQW(SEQ ID NO:111).

In a preferred embodiment the fluorette will bind to Rhodamine. Suitable fluorettes in this embodiment include, but are not limited to, IPHPPMYWTRVF (SEQ ID NO:3); IPHRPMYWTPVF (SEQ ID NO:22); and LPHPPMY-WTRVF (SEQ ID NO:23).

In a preferred embodiment the fluorette will bind to Oregon Green 514. Suitable fluorettes in this embodiment include, but are not limited to, HGWDYYWDWTAW (SEQ ID NO:4); ASDYWDWEWYYS (SEQ ID NO:5); YPND-FEWWEYYF (SEQ ID NO:6); HTSHISWPPWYF (SEQ ID NO:7); LEPRWGFGWWLK (SEQ ID NO:8); QYYG-WYYDHNFW (SEQ ID NO:9); YMYDEYQYWNFW (SEQ ID NO:10); HEWEYYWDWTAW (SEQ ID NO:24); HEWDYYWDWTAW (SEQ ID NO:25); HGWDYYWD-WTDW (SEQ ID NO:26); HGWDYYWWDWTPW (SEQ ID NO:27); HGWDYYWDWTTW (SEQ ID NO:28); HGWDYNWDWTAW (SEQ ID NO:29); and QGWDYY-WDWTAW (SEQ ID NO:30).

In a preferred embodiment the fluorette will bind to Fluorescein. Suitable fluorettes in this embodiment include, but are not limited to, YPNDFEWWEYYF (SEQ ID NO:6); ASDYWDWEWYYS (SEQ ID NO:5); WYDDWND-WHAWP (SEQ ID NO:11); WHMSPSWGWGYW (SEQ ID NO:12); HMSWWEFYLVPP (SEQ ID NO:13); YWDYS-WHYYAPY (SEQ ID NO:14); YPNEFDWWDYYY (SEQ ID NO:31); YPNDFEWWDYYY (SEQ ID NO:32); YHNDYEWWEYYY (SEQ ID NO:33); YPNDFEW-WEYYY (SEQ ID NO:34); YPNDFDWWEYYL (SEQ ID NO:35); YTHDYEWWEYYF (SEQ ID NO:36); YPNDYEWWEYYF (SEQ ID NO:37); YPSDFEW-WEYYF (SEQ ID NO:38); YHDFEWWEYYF (SEQ ID NO:39); and YPYDFEWWEYYM (SEQ ID NO:40).

Included within the definition of fluorettes are derivative or variant fluorettes. Accordingly, as used herein, a peptide is a fluorette if the overall homology of the peptide sequence to the amino acid sequences shown above (SED ID NOS 1-40 and 104-110) is preferably greater than about 70%, more preferably greater than about 75% even more preferably greater than about 80% and most preferably greater than about 90%, with homologies of greater than 95 to 98% being especially preferred. Homology in this context means sequence similarity or identity, with identity being preferred.

This homology will be determined using standard techniques known in the art, including, but not limited to, the local homology algorithm of Smith & Waterman, Adv. Appl. Math. 2:482 (1981), by the homology alignment algorithm of Needleman & Wunsch, J. Mol. Biool. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387-395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403-410, (1990) and Karlin et al., PNAS USA 90:5873-5787 (1993). A particularly useful BLAST program is the WU-BLAST-2 program which was obtained from Altschul et al., *Methods in Enzymology*, 266: 460480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "shorter" sequence in the aligned region. The "longer" sequence is the one having the most actual residues in the aligned region (gaps introduced by WU-Blast-2 to maximize the alignment score are ignored).

An additional useful algorithm is gapped BLAST as reported by Altschul et al. Nucleic Acids Res. 25:3389-3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A percent amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Alternatively, percent sequence identity is determined by inspection in which only identities are scored positively (+1) and all forms of sequence variation including gaps are assigned a value of "0". Percent sequence identity can be calculated, for example, by dividing the number of matching identical residues by the total number of residues of the "shorter" sequence in the aligned region and multiplying by 100. The "longer" sequence is the one having the most actual residues in the aligned region.

Once identified, the amino acid sequences of the fluorettes may be modified as needed. Sequence modifications include substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the fluorette are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function are made by selecting substitutions that are less conservative than those shown in Chart I, although these generally are not preferred. For example, substitutions may be made which more significantly affect the structure of the fluorette backbone in the area of the alteration, for example the alpha-helical or beta-sheet structure; the charge or hydrophobicity of the molecule; or the bulk of the side chain. The substitutions which in general are expected to produce the greatest changes in the fluorette's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

In a preferred embodiment, not more than about three substitutions or deletions will be made, and that the change will not be more than about 20 number %, usually not more than about 10 number %, of the number of amino acids in the fluorette, although in some instances higher numbers of alterations may be made.

Similarly, if the function or affinity of the fluorette is to be decreased, the amount of changes may also be greater. Preferred are conservative substitutions, as known in the art, including substitutions within the large hydrophobic group: isoleucine, leucine, valine and phenylalanine; between serine and threonine; glycine and alanine; asparagine and glutamine; aspartic acid and glutamic acid; or lysine, arginine and histidine. In some embodiments, non-conservative alterations are done.

As will be appreciated by those skilled in the art, a number of methods exist for the creation, isolation, or selection of fluorettes from a library of sequences (Oldenburg et al. Proc. Natl. Acad. Sci. U.S.A. 89:5393-5397 (1992); Scott et al., Proc. Natl. Acad. Sci. U.S.A. 89:5398-5402 (1992); Cull et al., Proc. Natl. Acad. Sci. U.S.A. 89:1865-1869 (1992); Devlin et al. Science 249:404-406 (1990); Schatz. Biotechnology 11:1138-1143 (1993)). In preferred embodiments, such libraries are based on, for example, either bacteriophage (Matthews and Wells. Science 260:1113-1117 (1993); Koivunen et al. Biotechnology 13:265-270 (1995); Yu and Smith. Methods Enzymol. 267:3-27 (1996); Harrison et al. Methods Enzymol. 267:83-109 (1996); Rebar and Pabo. Science 263:671-673 (1994); Rebar et al., Methods Enzymol. 267:129-149 (1996); Saggio and Laufer. Biochem. J. 293:613-616 (1993); Katz. Biochemistry 34:15421-15429 (1995); Caparon et al. Mol. Divers. 1:241-246 (1996); Parmley and Smith. Gene 73:305-318 (1988)), for example M13 or plasmids (Cull et al. Proc. Natl. Acad. Sci. U.S.A. 89:1865-1869 (1992); Schatz et al. Methods Enzymol. 267: 171-191 (1996); ) or polysomes (Mattheakis et al. Proc. Natl. Acad. Sci. U.S.A. 91:9022-9026; Hanes and Pluckthun Proc. Natl. Acad. Sci. U.S.A. 94: 49374942; Roberts and Szostak. Proc. Natl. Acad. Sci. U.S.A. 94:12297-12301)) Alternatively, peptide libraries can be expressed on the surface of a eukaryotic or prokaryotic cell and directly bound to a fluorophore dye and sorted, for example, by FACS. Alternatively, the cell expressing a fluorette is bound to a fluorophore dye that is bound to bead or a magnetic bead and purified and amplified as known in the art.

In a preferred embodiment, fluorettes are created, isolated, or selected from aptamer library phage display approaches. Such libraries are based on, for example, M13 filamentous bacteriophage (Smith. Science. 228:1315-1317 (1985); Cwirla et al. Proc. Natl. Acad. Sci. U.S.A. 87:6378-6382 (1990); Devlin et al. Science 249:404406 (1990); Scott and Smith. Science 249:386-390 (1990)) In a preferred embodiment, fluorettes are identified by screening a phage display peptide library that contains a combinatorial library of peptides interposed between the leader sequence and the amino terminus of mature form of bacteriophage M13amp9 minor coat protein, pIII.

The recombinatorial library can be produced by a number of methods as known in the art. In a preferred embodiment, the library is produced by annealing and cloning an oligonucleotide library of sequences into the M13amp9 pIII gene. Annealing of the oligonucleotide library to produce double-stranded DNA preferably produces "sticky ends" to facilitate directional cloning into the appropriate reading frame of the M13amp9. Alternatively, the annealed oligonucleotide library contains unique restriction enzyme sites, which are digested to produce "sticky ends" to facilitate directional cloning. The oligonucleotide library preferably also encodes an in-frame linker, tethering sequence, or spacer as described herein. The function of the linker is to decrease or minimize steric hindrance and promote accessibility of the fluorette for its fluorophore dye. The linker also promotes structural and functional independence of the fluorette. Phage particles bearing the peptide library are produced by introducing the M13amp9 vector into a permissive bacterial host, such as, *Escherichia coli* and other gram negative bacteria. According to the above strategy for cloning the peptide library, during phage maturation, the leader secretory sequence of pIII is removed, resulting in the peptide library sequence positioned immediately at the amino-terminus of the mature protein.

Cloning and expression of the oligonucleotide library produces a library of peptides either directly fused to the pIII protein or, preferably, fused via a linker or spacer. The linker or spacer can be, for example, sequence, as described herein, interposed between the fluorette and the pIII protein sequences.

The nucleic acids which give rise to the fluorettes are chemically synthesized, and thus may incorporate any nucleotide at any position. Thus, when the nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized nucleic acids and peptides. In an alternative embodiment, random DNA fragments may be made from fragmentation of genomic DNA, followed by sizing, and ligation into an appropriate vector for expression and selection.

The library should provide a sufficiently structurally diverse population of randomized expression products to effect a probabilistically sufficient range to allow isolation of a fluorette. Accordingly, a library must be large enough so that at least one of its members will have a structure that gives it affinity for a fluorophore dye. Although it is difficult to gauge the required absolute size of a library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide from about 7 to 20 amino acids in length has the potential to code for $20^7$ ($10^9$) to $20^{20}$. Thus, with libraries of $10^7$ to $10^8$ per ml of phage particles the present methods allow a "working" subset of a theoretically complete interaction library for 7 amino acids, and a subset of shapes for the $20^{20}$ library. Thus, in a preferred embodiment, at least $10^6$, preferably at least $10^8$, more preferably at least $10^{10}$ and most preferably at least $10^{12}$ different expression products are simultaneously analyzed in the subject methods. Preferred methods maximize library size and diversity.

It is important to understand that in any library system encoded by oligonucleotide synthesis one cannot have complete control over the codons that will eventually be incorporated into the peptide structure. This is especially true in the case of codons encoding stop signals (TAA, TGA, TAG). In a synthesis with NNN as the random region, there is a 3/64, or 4.69%, chance that the codon will be a stop codon. Thus, in a peptide of 10 residues, there is an unacceptable high likelihood that 46.7% of the peptides will prematurely terminate. For free peptide structures this is perhaps not a problem. But for larger structures, such as those envisioned here, such termination will lead to sterile peptide expression.

To alleviate this, random residues are encoded as NNK, where K=T or G. This allows for encoding of all potential amino acids (changing their relative representation slightly), but importantly preventing the encoding of two stop residues TAA and TGA. Thus, libraries encoding a 10 amino acid peptide will have a 15.6% chance to terminate prematurely. For candidate nucleic acids which are not designed to result in peptide expression products, this is not necessary. In one embodiment, the library is fully randomized, with no sequence preferences or constants at any position.

Once generated a peptide library is screened for binding to a fluorescent dye. In a preferred embodiment, bacteriophage expressing fluorettes are selected by biopanning, which consists of four sequential steps: i) phage binding with a fluorophore dye carrier, ii) removal of unbound or weakly bound phage, iii) elution of bound phage and (iv) amplification of bound phage. Certain steps can be omitted, for example, such as washing and amplification if the peptide library is expressed in eukaryotic or mammalian cells and fluorescence is detected and cells are shorted according to fluorescence or spectral shifts. If necessary or desirable, the amplified phage are used for the subsequent round(s) of biopanning against the corresponding fluorophore dye carrier until apparent enrichment for binding is observed over background. Preferably, after about four rounds of biopanning, phage bearing sequences that bind specifically to a fluorophore dye can be identified. Following biopanning, the individual phage are isolated, amplified and the sequence of the fluorette can be determined by various methods as known in the art. In another embodiment, eukaryotic or prokaryotic cells expressing a peptide library on their surface can be sorted by FACS and/or magnetic beads to isolate cells expressing fluorettes.

For biopanning, the fluorophore dyes can be bound to solid-phase carriers. In a preferred embodiment, the dyes are covalently attached to a target bead. This facilitates washing and removal of non-specifically bound or weakly bound phage. Preferably, a linker or spacer molecule is interposed between the fluorophore dye and the target bead, for example, succinimidy esters and derivatives of fluorophores. A spacer molecule increases the accessibility of the fluorophore dye and minimizes potential steric hindrance that may interfere with the interactions between the fluorophore dye and the bacteriophage particles that bear the peptide library. The number of fluorophore dye molecules bound to the carrier will vary. In general, there are up to about 1 micromole. Higher or lower amounts of dye can be attached per ml of carrier beads, as needed, for example to increase or decrease the stringency of the biopanning conditions.

Once a fluorette is identified, it can be mutagenized or derivatized to isolate fluorettes with altered properties. In a preferred embodiment, the derivatize fluorettes have a higher affinity or specificity, thereby, providing, for example, increased sensitivity for the assay or system in which the fluorette is employed. This also allows the use of lower amounts of fluorescent dye, thereby, limiting toxicity of the fluorescent dye to cells, if needed.

In a preferred embodiment, affinity maturation (Yu and Smith. supra) can be used to produce mutant or derivative fluorettes with improved affinities over their corresponding parental fluorettes. To create, select or isolate fluorettes with a higher affinity, a second oligonucleotide library is produced that is, preferabbly, based. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the amino acid sequences of the fluorettes are subjected to biased mutagenesis at a desired mutagenesis rate using a number of methods as known in the art. The sequences can be mutagenized by systematic alteration of the codons encoding the fluorettes. Oligonucleotide mutagenesis, is preferablly, performed during the synthesis of the oligonucleotide library. To increase the probability that all amino acids will be represented at each position and to limit the generation of stop codons within the fluorette encoding sequences, specific nucleotides, such as A and C, can be omitted from the third position of each codon. As described above, the oligonucleotide library is preferably annealed and cloned into an expression vector of choice.

To select fluorettes with higher binding affinity than the parental fluorette, the biopanning conditions are preferably altered to be more stringent by, for example, changing one or more of the following conditions. This also provides a method to maximize selection against the parental fluorette. To increase the stringency of the biopanning, the concentration of the fluorophore dye bound to the carrier beads can be decreased. In addition, the phage concentration represented in the binding step and/or the binding time also can be reduced. Alternatively, the stringency of the washing conditions is increased. Washing stringency can be increased by, for example, increasing the volume of washing buffer per ml of carrier beads, increasing the wash temperature, altering the ionic strength or pH of the wash buffer, increasing the detergent concentration or by using a stronger, ionizing detergent. (Sambrook et al., (1989) Molecular Cloning: A Laboratory Manual (2nd Edition). Cold Spring Harabor Laboratory, Cold Spring Harbor, N.Y.). Other parameters that can be altered to increase stringency are, for example, increasing the temperature and competition for binding to the fluorophore dye by related molecules.

Fluorette binding to a fluorophore dye can be assessed in several ways. For example, when a phage display system is used, binding of the bacteriophage-bearing peptide library to the fluorophore dye-carrier can be determined by comparing the infectious particle titers of input phage to eluted phage. To measure phage-fluorophore dye binding in solution, a known concentration of free fluorophore dye is mixed with a known number of purified phage particles. The number of particles is preferably calculated from the optical densities of the purifed phage at 260 nm and 280 nm but other methods, such as, infectious titer can be used. Phage-fluorophore dye complexes are separated by, for example, precipitation to remove unbound dye, spotted onto a solid-support filter, such as, nitrocellulose and scanned for fluorescence. Other methods to remove unbound dye include, for example, competition with related molecules, washing, and increased stringency To determine nonspecific binding, controls using phage particles that do not display recombinatorial library sequences are run in parallel. In addition, specific to nonspecific binding ratios also can be quantitated.

Fluorette/fluorophore dye dissociation constants can be determined in several ways. For example, when a phage display system is used, phage-fluorophore dye dissociation constants can be determined by, for example, incubating for several hours subsaturating amounts of phage with a fluorophore dye bound to a carrier, for example, a bead as described above. The bead suspensions are removed, for example, by centrifugation, and the unbound phage in the supernatants can be titrated. Other methods for measuring unbound phage are known in the art, for example, visualization. Dissociation constants can be measured via a standard linear Scatchard plot. Nonspecific background binding is determined using phage that does not express fluorette sequences.

In a preferred embodiment, fluorettes are encoded by nucleic acids and produced by recombinant molecular biology techniques (Sambrook et al. (1989) Molecular Cloning: A Laboratory Manual (2nd Edition) Cold Spring Harbor Laboratory, Cold Spring Harbor, N.Y.; Ausubel et al. (1994) Current Protocols in Molecular Biology. Massachusetts General Hospital and Harvard Medical School. Boston, Mass.). Thus, the present invention provides nucleic acids encoding fluorettes. By "nucleic acids" herein is meant a nucleic acid, DNA or RNA depending on the delivery or expression vehicle or vector used, which can be manipulated to express fluorettes; that is, the nucleic acids encoding the fluorettes and the fusion partners and linkers if present. In addition, the nucleic acids will also generally contain enough extra sequence to effect translation or transcription, as necessary. For a fluorette, the nucleic acid generally contains cloning sites which are placed to allow in frame expression of the fluorettes, and any fusion partners, if present, such as presentation structures. For example, when presentation structures are used, the presentation structure will generally contain the initating ATG, as a part of the parent vector. For example, for retrovirus expression, the nucleic acids are generally constructed with an internal CMV promoter, tRNA promoter or cell specific promoter designed for immediate and appropriate expression of the fluorette at the initiation site of RNA synthesis. The RNA is expressed anti-sense to the direction of retroviral synthesis and is terminated as known, for example with an orientation specific terminator sequence. Interference from upstream transcription is alleviated in the target cell with the self-inactivation deletion, a common feature of certain retroviral expression systems. In another embodiment, other expression vectors or systems also can be used, such as, adenovirus, adenoassociated virus, or transposons.

Generally, the nucleic acids are introduced and expressed within the cells to produce fluorettes. By "introduced into " or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®, electroporation, viral infection, etc. The candidate nucleic acids may stably integrate into the genome of the host cell (for example, with retroviral introduction), or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

In a preferred embodiment the fluorettes functions within the cell in which they are expressed. Alternatively, fluorettes may be expressed within a cell or secreted from a cell, and purified. If desired, the fluorette can be introduced into another cell by electroporation, calcium phosphate precipitation, microinjectioin, liposome fusion, lipofectin, viral infection, etc. Fluorettes also may be produced in vitro by transcription/translation reactions. Alternatively, fluorettes are chemically synthesized using any of a number of methods.

In a preferred embodiment, the present invention provides a complex or composition of a fluorette bound to a fluorophore dye. The binding of the fluorette to the fluorophore dye leads to four possible outcomes in regards to the excitation and emission spectra of the fluorophore dye i) little to no change in the fluorophore emission or excitation spectra, ii) change in fluorophore emission, iii) change in fluorophore excitation and (iv) change in both fluorophore emission and excitations.

In one embodiment, binding of the fluorette to the fluorophore dye may prevent fluorophore excitation or emission. In either scenario, the fluorophore dye, no longer fluoresces when bound to the fluorette. In another embodiment, the excitation spectrum and/or the emission spectrum of the fluorophore dye is shifted, to a shorter or longer wavelength. Alternatively, the excitation spectrum and/or emission spectrum can be broadened.

In a preferred embodiment the excitation spectrum is altered up to about 5 nm, about 10 nm, being preferred, 20 nm particularly preferred, and about 100 nm being especially preferred.

Fluorettes in their various forms find use in detector systems and various types of assays and techniques using a large set of potential fluorophore dyes, for example as, in detection of viral delivery systems, diagnostics, high-throughput assays.

Once made, the compositions find use in a number of applications. These applications include binding a fluorophore dye to the fluorette, removing unbound dye and detecting fluorescence. In a preferred embodiment, the emission and/or excitation spectrum of the fluorophore dye is altered when bound to a fluorette. Therefore, it is not necessary to remove unbound dye. In a preferred embodiment, are applications that in some manner tethers the excitation and emission of two or more flourette/fluorescent dye complexes in such a way that they can be detected by fluorescence resonance energy transfer (FRET).

FRET applications based on fluorette/fluorophore dye interactions provide methods to demonstrate the proximity or interactions of two or more molecules. These molecules include, for example, biological molecules, such as proteins, lipids, nucleic acids, carbohydrates. In another embodiment, FRET can be applied to detect or induce the localized activation of a produrg In a preferred embodiment, the interactions of two or more proteins, each containing a unique fluorette sequence can be demonstrated as follows. First, the fluorophore dyes are bound by their corresponding fluorettes. Next, one of the fluorette/fluorophore dye complexes or donor complex is excited and fluoresces. When the two proteins containing the fluorette sequences are in close proximity or in some way have interacted, the emitted light of the first donor complex causes the second fluorette/fluorophore dye complex (acceptor) to fluoresce.

Another example of a FRET application employs fluorette/fluorophore dye complexes that are covalently or associately linked to target biomaterials via small ligands. The demonstration of FRET as described above indicates an interaction or the proximity of the target biomaterials when bound to their respective ligands. Other applications include, "trigger dependent FRET", in which the use and design of trigger molecules, such as, heavy metal ions, drugs, etc., that specifically bind to the ligand or target biomaterials, causing dissociation of one or more of the fluorette/dye complexes from the target biomaterials and a decrease or loss of FRET.

FRET may also be employed to detect intramolecular interactions or events, such as, changes in molecular structure that occurs in a molecule with the binding and/or dissociation of a ligand.

In FRET applications, double or higher order fluorettes may be linked, for example, via a rigid connector, such as polyalanine or polyserine, to provide the correct angle of orientation of corresponding donor and acceptor fluorette/fluorophore dye complexes. This may be of importance for efficient and quantitative FRET output. In some cases, it may be desirable for the spacer to contain a peptide sequence or other material which, upon binding a specific fluorophore dye, brings the donor and acceptor comlexes into proximity such that FRET can ensue.

FRET applications also include dual fluorophore dye quenching due to fluorette binding. For example, fluorettes specific for donor and acceptor fluorophores are joined by a protease cleavable spacer. This fluorette dimer is bound to its two fluorophore dyes targets and FRET ensues as described above. However, FRET decreases after protease cleavage of the fluorette dimer.

Other novel assays are based on fluorophore dye quenching due to its binding of a specific fluorette. For example, a target protein is labeled in vitro by a fluorophore dye and is assembled into a complex particle or structure with other materials (e.g., other proteins, DNA or RNA) whose conformation or structure is to be investigated. The addition of a specific fluorette after the complex is assembled and measuring fluoresence indicates if the fluorette had access (binding) or no access (no binding) to its target dye.

Novel reporter gene assays based on fluorette-induced Stokes shift changes also can be created. For example, a fluorette fused with a given carrier protein can be used as a gene activity reporter for the presence of the protein. Cell extracts, or living cells expressing the protein, can be monitored for fluorette activity when the specific fluorophore dye is bound by the peptide. Binding of the fluorophore dye by the fluorette/peptide modifies the excitation and/or emitted wavelength permitting specific detection of the expressed protein. Consequently, the more Stokes shift changes introduced by binding of peptide the more sensitive the assay can become. The simplicity of such an approach surpasses the currently available enzymatic reporter gene assays (e.g., luciferase and beta-galactosidase assays).

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references, patents, patent applications, and publications cited herein are incorporated by reference in their entirety.

EXAMPLE 1

Synthesis of Fluorophore Dye Carriers

Four fluorophore dyes, Texas Red, Fluorescein, Rhodamine Red and Oregon Green 514, were chosen, for selection of fluorettes from a phage display library (Example 2). The chemical structures of the dye conjugates are shown in FIG. 1. The first three dyes, Texas Red, Fluorescein and Rhodamine Red fall into one group: (i) they have a relatively high molar extinction coefficient for absorption and excellent quantum fluorescence yields (Haugland supra), (ii) they have non-overlapping spectral characteristics, (iii) they have the potential for cross-quenching and/or FRET analysis. The fourth dye, Oregon Green 514, related structurally to Fluorescein, was chosen to determine if structure-function relationships could be discerned between fluorette peptides that bound related dyes.

The extinction coefficient and quantum yield is important for sensitivity of detection and was a major factor determining choice of fluorophores. Fluorescence detection by the outlined approach, at its simplest conception, is stochiometric in nature. In addition, peptide binding of the target dye might lead to some fluorescence quenching. Finally, if fluorettes can be created that each can specifically bind different dyes then it is possible to measure proximal interactions between molecules by FRET relative to the binding of specific dyes having accommodating overlapping fluorescence spectra.

Succinimidyl esters of the four chosen fluorophore dyes (with 3- or 7-atom spacer between the dye molecule and the reactive succinimidyl group) were separately and covalently linked to target beads. Linkages were established through the formation of a stable peptide bond to UltraLink Immobilized DADPA carrier beads (capacity—45 µMoles of free amino groups per ml of beads) containing a 12-atom diaminodipropylamine spacer and a terminal amino-group (Pierce). Activated derivatives of fluorophore dyes: 6-(fluorescein-5-(and-6)-carboxamido)hexanoic acid, succinimidyl ester (5(6)-SFX), "mixed isomers"; Oregon Green 514 carboxylic acid, succinimidyl ester; Rhodamine Red-X, succinimidyl ester, "mixed isomers" and Texas Red-X, succinimidyl ester, "mixed isomers" were purchased from Molecular Probes.

Covalent coupling of activated derivatives of fluorophore dyes to a polymer carrier was performed in accordance with both manufacturer's protocols, with some modifications. Briefly, 1 ml of each dye derivative (5 mg/ml in anhydrous dimethylformamide) was separately mixed with 15 ml of 50% slurry of UltraLink Immobilized DADPA in 0.2M sodium bicarbonate buffer, pH 8.3 (the coupling yield was at least 95% and, consequently, four fluorophore dye carriers contained 0.7-1 µMoles of covalently bound dyes per ml of beads), unreacted amino groups of the carriers were extensively acetylated by an addition of 18-fold molar excess of acetic acid N-hydroxysuccinimide ester (Sigma) followed by hydroxylamine treatment of the fluorophore dye carriers in order to destroy any unstable intermolecular intermediates of fluorophore dyes via their hydroxyl groups (for Fluorescein- and Oregon Green 514 carriers only). Finally, fluorophore dye carriers were quenched in 0.75M Tris-HCl, pH 8.7, loaded to the columns and extensively washed in high salt buffer, 50 mM Tris-HCl, pH 7.5+1M NaCl followed by a storage buffer, 50 mM Tris-HCl, pH 7.5+150 mM NaCl (TBS)+0.05% sodium azide. Fluorophore dye carriers were stored as 50% slurries at 4° C.

The chemical structures of the dye conjugates are shown in FIG. 1. The resulting total spacer between the dye molecule and polymer carrier was 19-atoms long for Texas Red-, Fluorescein-, Rhodamine Red-conjugates and 15-atoms long for Oregon Green 514-conjugate. This allows maximal reduction of steric hindrance for potential interactions with the large bacteriophage particles that bear the peptide libraries. After preparation we determined that the fluorophore dye carriers contained from 0.7-1 µMoles of covalently bound dye per ml of carrier beads.

EXAMPLE 2

Selection for Peptide Aptamers that Bind Small Molecule Fluorophores

A phage display peptide library was screened that contained a combinatorial library of 12-mer peptides fused via a short glycine linker spacer (GGG) to the amino-terminus of a minor coat pIII protein (5 copies per particle, Li et al. (1980) J. Biol. Chem. 255:10331-10337) of the filamentous bacteriophage M13mp19 (Ph.D. phage display, New England Biolabs). During phage maturation, the leader secretory sequence is removed. This results in the 12-mer peptide positioned immediately at the amino-terminus of the mature protein.

E. coli ER2537 strain [F' lacI$^q$ Δ(lacZ)M15 proA$^+$B$^+$/ fhuA2 supE thi Δ(lac-proAB) Δ(hsdSM-mcrB)5 (rk$^-$ mk$^-$ mcrBC$^-$)] and E.coli TG-1 strain [supE thi-1 Δ(lac-proAB) Δ(mcrB-hsdSM)5 (rk$^-$ mk$^-$) (F' traD36 proAB lacI$^q$ZΔM15)] were purchased from New England Biolabs and Stratagene, respectively, and used as bacteriophage M13mp19 hosts. All bacteriological techniques were performed as described (Sambrook et al., supra; Ausubel et al., supra).

Each biopanning round consisted of four sequential steps: (i) phage binding with a fluorophore dye carrier, (ii) washing unbound phage from the beads, (iii) nonspecific elution of bound phage and (iv) amplification of bound phage. The Ph.D.-12 phage display peptide library (based on modified M13mp19 bacteriophage, $1.9 \times 10^9$ independent transformants) as a part of the Ph.D.-12 phage display peptide library kit was purchased from New England Biolabs. All procedures were carried out at room temperature unless noted. First, 0.15 ml of centrifuged fluorophore dye carrier beads were blocked with 3 ml of TBS+2 mg/ml BSA (blocking buffer) for 1.5 hr with gentle rotating, beads were washed with 15 ml TBS+0.1% Tween-20+0.5 mg/ml BSA (binding buffer), centrifuged, mixed with $1.8 \times 10^{11}$ plaque-forming units (pfu) of the Ph.D.-12 phage display peptide library (~95-fold library size) in 3 ml of binding buffer and suspension was gently rotated for 4 hr. For washing, bead suspensions were centrifuged and beads were transferred to the microcolumns and slowly washed by 100-fold beads volume of TBS+0.1% Tween-20. The bound phage were nonspecifically eluted by 1 ml of 0.2M glycine-HCl, pH 2.2+1 mg/ml BSA (elution buffer) for 10' and the eluates were immediately adjusted to a neutral pH by 0.15 ml of 1M Tris-HCl, pH 9.1. Bound phage yields were determined by a titration of the eluates on the ER2537 host strain (Sambrook et al., supra). Amplification step: all bound phage (1.1 ml) were added to 27 ml of 1/100 diluted overnight ER2537 culture and amplified for 4.5 hr at 37° C. with vigorous shaking. The amplified phage were precipitated from cell supernatants by 1/5 V of 20% PEG+2.5M NaCl at 4° C., re-precipitated again and, finally, suspended in 0.5 ml TBS+ 0.05% sodium azide. The resultant ~50-fold concentrated amplified phage were stored at 4° C. and their titers usually were in the range $0.5$-$1.5 \times 10^{13}$ pfu/ml. For long-term storage amplified phage were adjusted to 50% glycerol and stored at −20° C.

Figure 2:
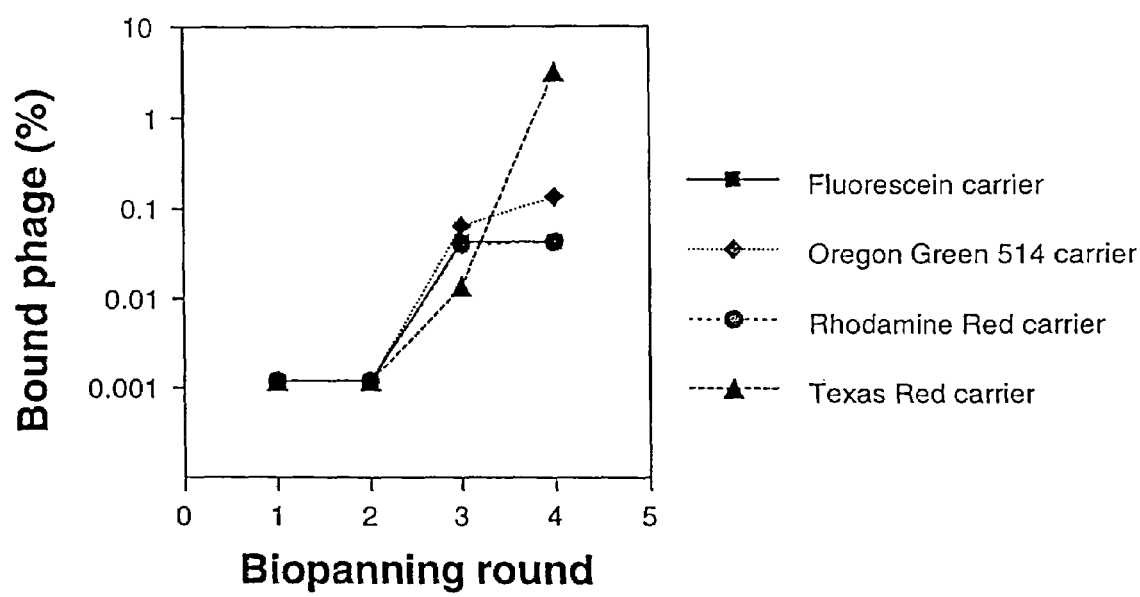
FIG. 2. Biopanning with a peptide phage display library against Fluorescein, Oregon Green 514, Rhodamine Red and Texas Red carriers. A Ph.D.-12 phage display peptide library (New England Biolabs) is a combinatorial library of 12-mer peptides fused to the amino-terminus of a minor coat pIII protein of the bacteriophage M13mp19. Bound phage in four biopanning rounds were calculated as a percentage of eluted phage plaque forming unit (plaque forming unit (pfu)) yield vs input phage plaque forming unit (pfu). All experiments were performed in duplicate. Standard deviations did not exceed 19%.

The amplified phage were used for the next biopanning rounds against the corresponding fluorophore dye carrier, if necessary, until apparent enrichment for binding was observed over background. We observed a significant increase in the amounts of bound phage after 3-4 rounds of biopanning (for all of the fluorophore dye carriers see FIG. 2). This was compared to the nonspecific phage background in the first and second biopanning rounds. Eluted phage from round 4 selected against four different fluorophore dye carriers are termed herein as TR-4, RhR4, OG-4 and Flu-4 (standing for Texas Red, Rhodamine Red, Oregon Green 514 and Fluorescein carriers, respectively).

The amplified phage from round 1 were further selected against the corresponding fluorophore dye carrier. The next biopanning rounds were performed in the same manner as round 1, except that: (i) input phage in the binding reaction were increased to $4.5 \times 10^{11}$ pfu, (ii) time of binding was reduced to 2 hr in round 4, (iii) Tween-20 concentration in a washing buffer was increased to 0.2% in round 3 and 0.4% in round 4, (iv) eluted phage from last round 4 were not amplified, but rather served as a source of independent phage clones used for sequencing.

The TR-4, RhR-4, OG-4 and Flu-4 phage sets were used as a source of independent phage clones that were sequenced for further analysis. Phage single-stranded DNAs (ss DNAs) only a polymer linker moiety of Texas Red and Rhodamine Red carriers or other chemical features of the carriers themselves.

TABLE 1

Fluorophore dye-specific phage clones and peptide fluorette sequences.

| Fluorophore dye carrier | Phage clone[a] | Phage clone frequency | Fluorette | Fluorette consensus[b] | Fluorette net charge[c] | Fluuorette hydrophobicity[d] |
|---|---|---|---|---|---|---|
| Texas Red | TR401[e] | 5/6 | KHVQYWTQMFYS | unique sequence | +1 | 5/12 |
|  | TR406 | 1/6 | DFLQWKLARQKP | (with a single exception) | +2 | 5/12 |
| Rhodamine Red | RhR401[e] | 6/6 | IPHPPMYWTRVF | unique sequence | +1 | 5/12 |
| Oregon Green 514 | OG403[e] | 4/12 | HG<u>WDYYWDW</u>TAW | <u>YWDW</u> | −2 | 7/12 |
|  | OG401[e] | 2/12 | ASD<u>YWDW</u>EWYYS | W(D/E)YY | −3 | 7/12 |
|  | OG402[e] | 2/12 | YPNDFEW<u>WEYY</u>F | <u>YY</u> | −3 | 7/12 |
|  | OG409 | 1/12 | HTSHISWPPWYF | <u>NFW</u> | 0 | 5/12 |
|  | OG410 | 1/12 | LEPRWGFGWWLK |  | +1 | 6/12 |
|  | OG411 | 1/12 | Q<u>YY</u>GW<u>YY</u>DH<u>NFW</u> |  | −1 | 7/12 |
|  | OG412 | 1/12 | YMYDEYQYW<u>NFW</u> |  | −2 | 7/12 |
| Fluorescein | OG402[e] | 7/14 | YPNDFEWWE<u>YY</u>F | <u>YY</u> | −3 | 7/12 |
|  | OG401[e] | 2/14 | ASDYWDWEW<u>YY</u>S |  | −3 | 7/12 |
|  | Flu406[e] | 2/14 | WYDDWNDWHAWP |  | −3 | 6/12 |
|  | Flu404 | 1/14 | WHMSPSWGWGYW |  | 0 | 5/12 |
|  | Flu405 | 1/14 | HMSWWEFYLVPP |  | −1 | 6/12 |
|  | Flu413 | 1/14 | YWDYSWH<u>YY</u>APT |  | −1 | 7/12 |

[a]phage clones were isolated after four biopanning rounds with random combinatorial Ph.D.-12 phage display peptide library (see text),
[b]partial consensus (shown underlined) for Oregon Green 514- and Fluorescein-specific peptide fluorettes, (YWDW (SEQ ID NO: 113); W(D/E)YY (SEQ ID NO: 114)
[c]−1 (D, E) or +1 (K, R),
[d]number of hydrophobic amino acids (A, V, L, I, W, Y, F) per total number of peptide fluorette amino acids,
[e]phage clone is represented in the corresponding group at least twice.

and double-stranded DNAs (ds DNAs) were purified as previously described (Sambrook et al., supra). Fluorette-coding portions of the DNA and adjacent DNA regions were sequenced with −96 gIII sequencing primer CCCTCAT-AGTTAGCGTAACG (New England Biolabs) (SEQ ID NO:115) using an Applied Biosystems 391 automated DNA sequencer.

The sequences from the insert regions of the phage are grouped in Table 1. Two unique sequences were found that bound to the Texas Red conjugate beads, one for Rhodamine Red, seven for Oregon Green, and six for Fluorescein. Note that the Oregon Green set and the Fluorescein set shared two sequences that were identical at the nucleotide level as well as the amino acid sequence presented. These and other issues relevant to such observations are explored later.

Phage selected against the Texas Red carrier gave rise to the sequences KHVQYWTQMFYS and DFLQWKLAR-QKP at a 5:1 ratio (Table 1). Biopanning with the phage display library against the Rhodamine Red carrier gave rise to a single phage clone, RhR401, carrying the amino acid sequence IPHPPMYWTRVF. Thus, TR-4 and RhR-4 phage sets may be considered to be nearly "pure" phage clone populations by the fourth round of selection.

We tested the binding specificity and excluded the possibility that the TR401 and RhR401 phage were selected against the polymer linker moiety rather than a fluorophore dye moiety of the dye carriers. The TR-4 and RhR-4 phage were cross-bound to Rhodamine Red and Texas Red carriers, respectively. Cross-binding of each phage to the inappropriate dye carrier did not exceed the nonspecific phage background binding (data not shown). Thus the TR401 and RhR401 fluorettes are specific by this comparison for their respective conjugated dyes, despite the similarity of the compound core ring structures. Second, they had affinity for the corresponding conjugated fluorophore dyes rather than Four rounds of biopanning with the phage display peptide library against Oregon Green 514 and Fluorescein carriers were undertaken. Three clones were predominant in the sequenced population selected against Oregon Green (OG401, OG402, OG403) and four clones were represented once (Table 1). Similarly, when selected against Fluorescein three clones predominated and others were represented only once. Notably two of the three predominant Fluorescein-specific fluorettes had the same sequence as two of the predominant, independently selected fluorettes that had been found with the Oregon Green 514 carrier. These were OG402 fluorette (YPNDFEWWEYYF) and the OG401 fluorette (ASDYWDWEWYYS). Since Oregon Green 514 is structurally related to Fluorescein, and is considered a Fluorescein pentafluoride (see FIG. 1), independent selection of the same peptide fluorettes against Oregon Green 514 and Fluorescein carriers was predicted. The same fluorettes selected independently against these fluorophores possibly bind to similar domains of the Oregon Green 514 and Fluorescein dye molecules.

The selected phage had been originally selected as being capable of binding fluorophore dyes that had been covalently linked to a polymer carrier. The nature of carrier-crosslinked fluorophores, while useful for initial selection of phage, is inappropriate to study affinity of the phage except in relative terms. We therefore tested whether the selected phage can bind to the corresponding free fluorophore dyes in solution. Each bacteriophage particle contains 5 copies of pIII-fluorette fusion protein. Therefore phage binding is governed by avidity considerations. We bound free fluorophore dyes to highly concentrated phage solutions and assayed for bound fluorophore dye after precipitation of the phage.

Four activated derivatives of fluorophore dyes (see above) were quenched in 0.5M Tris-HCl, pH 8.7 and used as "free"

dyes. Ten µl of PEG-purified and 300-fold concentrated phage TR401, RhR401, OG402, OG403 (1.3-1.8×10$^{12}$ phage particles; calculated from optical densities of the purified phage at 260 and 280 nm) in TBS+0.05% sodium azide buffer were separately mixed with an equal volume of 20 µM solution of the corresponding free dyes in the same buffer; mixtures were adjusted by Tween-20 to 0.1% and incubated for 3 hr. Phage-fluorophore dye complexes were precipitated three times by PEG-8000 in order to remove unbound dye and dissolved in 6.6 µl of TBS+0.05% sodium azide buffer. Finally, phage-fluorophore dye complexes (1 µl of each) were spotted to nitrocellulose filter and filter was scanned on the Storm 840 scanner (Molecular Dynamics) in Blue Fluorescence/Chemifluorescence mode with 200µ pixel resolution. To determine nonspecific binding the nor-well as the predominant Oregon Green 514- and Fluorescein-specific fluorette clones (OG403 and OG402, respectively, see above), for this forced evolution based on initial indications of their affinities (data not shown). We set up oligonucleotide synthesis of the corresponding fluorette-coded DNA sequences in such a manner that the mutagenesis rate was 9% for every 36 nucleotide positions of the peptide fluorette. Nucleotides A and C were omitted from the third position in each codon to improve the relative representation of all amino acids and by limits stop codon generation.

Four minus-strand oligonucleotides containing degenerated fluorette-coding sequences were synthesized (Protein & Nucleic Acids Facility, Stanford University Medical Center),

```
TR401-91CL:
CTCCCCTTCGGCCGAACCTCCACCAGAATAAAACATCTGCGTCCAATACTGCACATGCTTA    (SEQ ID NO:88)

GAGTGAGAATAGAAAGGTACCACTCTCCC;

RhR401-91CL:
CTCCCCTTCGGCCGAACCTCCACCAAACACACGAGTCCAATACATAGGAGGATGCGGAAT    (SEQ ID NO:89)

AGAGTGAGAATAGAAAGGTACCACTCTCCC;

OG402-91CL:
CTCCCCTTCGGCCGAACCTCCACCAAAATAATACTCCCACCACTCAAAATCATTCGGATAA    (SEQ ID NO:90)

GAGTGAGAATAGAAAGGTACCACTCTCCC;

OG403-91CL:
CTCCCCTTCGGCCGAACCTCCACCCCAAGCAGTCCAATCCCAATAATAATCCCACCCATGA    (SEQ ID NO:91)

GAGTGAGAATAGAAAGGTACCACTCTCCC.
``` malized amounts of phage particles of amplified, unselected, and PEG-purified Ph.D.-12 phage display peptide library were separately incubated with the corresponding free dyes and treated in the same conditions. All binding experiments were accomplished in duplicate. Specific/nonspecific signal ratios were quantified by densitometry of spot images using "Measure" option of NIH Image 1.59 freeware package.

Figure 3:
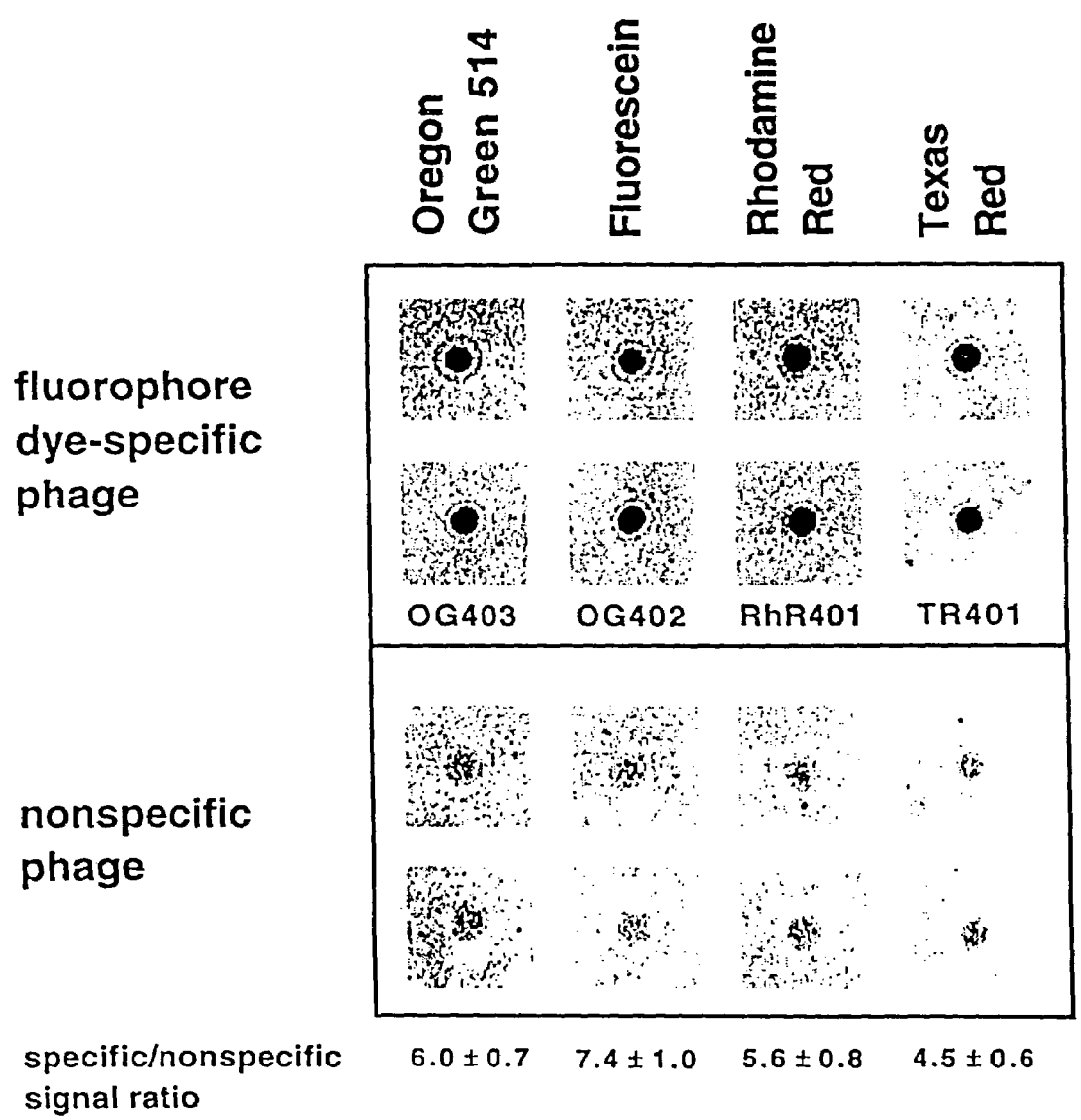
FIG. 3. Phage-fluorophore dye binding. Fluorophore dye-specific OG403, OG402, RhR401 and TR401 phage were bound to Oregon Green 514, Fluorescein, Rhodamine Red and Texas Red "free" dyes, respectively (see text). The normalized particle amounts of amplified Ph.D.-12 phage display peptide library (nonspecific phage) were bound in solution with the same dyes as controls. Phage-fluorophore dye complexes were precipitated three times by PEG to remove unbound dye and spotted to a nitrocellulose filter. The filter was scanned on the Storm 840 scanner (Molecular Dynamics). The presented data is from a single scan and image enhancements were done simultaneously on the complete set of dye binding results using NIH Image 1.59 software. Specific/nonspecific signal ratios were quantified by densitometry of spot images using NIH Image 1.59 software (see Materials and Methods for details). All binding experiments shown were completed in duplicate. Densitometry was carried out prior to contrast enhancement. Brightness and contrast values were modified to 50 and 65, respectively in Adobe Photoshop. Individual elements of the figure were arranged as a composite from the same original scan from which the binding ratios were determined.

We found that OG403, OG402, RhR401 and TR401 phage specifically bound their respective fluorophore dyes (see FIG. 3). This result shows that phage selected against covalently bound fluorophore dye were still capable of interacting with their cognate free fluorophore dye in solution.

EXAMPLE 3

Forced Evolution of Higher Affinity Fluorophore-Binding Peptides

The total number of possible random 12-mer peptides is equal to $20^{12}=4.1\times10^{15}$. The complexity of the phage display peptide library used for biopanning against the fluorophore dye carriers was much smaller, containing only $1.9\times10^9$ clones. Thus, the library represents a fraction of all possible 12-mer peptides that could have been searched for binding. We therefore sought to improve the present fluorettes. We chose to introduce mutations into the fluorette peptide sequences at the DNA level in the phage and then select for phage that displayed peptides with higher affinity (compared to the parent) against the respective fluorophore dye carrier. We chose the Texas Red- and Rhodamine Red-specific clones (TR401 and RhR401, respectively), as Nucleotides in a regular case shows no degeneracy; boldfaced nucleotide designates 91% of shown nucleotide and 3×3% of each of the other three nucleotides; boldfaced and underlined nucleotide designates 91% of A or C and 9% of C or A, respectively.

Degenerated minus-strand oligonucleotides were separately annealed to the plus-strand oligonucleotide GGGAGAGTGGTACCTTTCTATTCTCAC (SEQ ID NO:92), partial duplexes were filled by T4 DNA Polymerase (Ausubel et al., supra), cut by KpnI and EagI and, finally, 1.9 ng of double digested filled duplexes was ligated to 200 ng of low-melting point agarose gel-purified large fragment of the replicative form (RF) Ph.D.121 DNA cut with the same pair of enzymes (the Ph.D.121 was a randomly picked phage clone from the Ph.D.-12 phage display peptide library) in a total volume 0.1 ml. Ligations were electroporated into 0.5 ml of TG-1 electrocompetent cells (Stratagene) according to manufacturer's protocol and phage library complexities were determined by immediate mixing of several 10-fold dilutions of transfected TG-1 cells with ER2537 cells and plating. Phage libraries were further amplified in 400 ml of liquid LB media for 4 hr at 37° C. with vigorous shaking, concentrated by PEG (see above) and, finally, suspended in 0.5 ml TBS+0.05% sodium azide buffer.

Titers of four resultant nonrandom combinatorial phage libraries were 0.2-4.0×10$^{13}$ pfu/ml. For a long-term storage phage libraries were adjusted to 50% glycerol and stored at −20° C. Twelve independent phage clones from each TR401-91CL and RhR401-91CL libraries were sequenced in order to determine the average level of amino acid substitutions in the fluorette moiety.

We determined the nucleotide sequences of twelve independent phage clones from each of the TR401-91CL and RhR401-91CL libraries in order to determine the average level of amino acid substitutions in the displayed fluorettes. These were determined to be 2.30 and 2.45, respectively. These experimental values correlated well to the expected theoretical values (calculated from a degeneration frequency 0.09 on the nucleotide level, see above). The nucleotide mutation rate from the other two libraries, OG403-91CL and OG402-91CL was not determined but likely had a comparable average level of amino acid substitutions in the fluorette moiety as all four corresponding oligonucleotides were synthesized in parallel using the same batch of pre-mixed monomer nucleotides.

A key difference of the secondary biopanning versus the primary biopanning with the original phage library is the strict need to maximize selection against the originating, parental fluorette. For this purpose we significantly reduced concentrations of the fluorophore dye carrier. We also reduced the phage concentrations present during the binding steps. In addition, the binding time was reduced while the amounts of washing buffer per ml of carrier beads were increased. Specifically, (i) input phage in the binding reaction were decreased to $1.0 \times 10^{10}$ pfu, (ii) time of binding was reduced to 10', (iii) amount of fluorophore dye carrier beads in the binding reaction was reduced to 0.03 ml, (iv) following binding to the phage beads were washed with 330-fold beads volume of washing buffer and (v) Tween-20 concentration in the washing buffer was increased to 0.4%.

Figure 4:
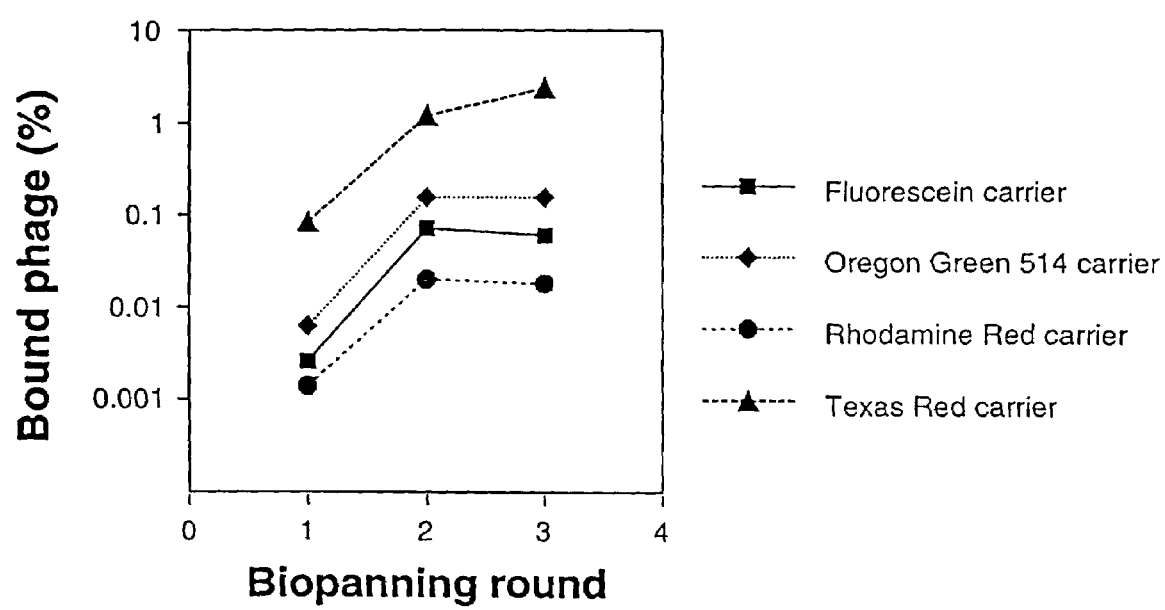
FIG. 4. Biopanning with four biased combinatorial phage display peptide libraries based on degenerated fluorettes against Fluorescein, Oregon Green 514, Rhodamine Red and Texas Red carriers. OG402-91CL, OG403-91CL, RhR401-91CL and TR401-91CL biased combinatorial phage display peptide libraries (see text) were subjected to a biopanning against Fluorescein, Oregon Green 514, Rhodamine Red and Texas Red carriers, respectively. Bound phage in three biopanning rounds were calculated as described in a legend to FIG. 2. All experiments were performed in duplicate. Standard deviations did not exceed 21%.

An increase in approximately 1.2-1.5 logs of magnitude in the total number of bound phage after 2-3 rounds of biopanning (compared to that of the first round) for all the fluorophore dye carriers was seen (see FIG. 4). Eluted phage from round 3 were termed TRS-3, RhRS-3, OGS-3 and FluS-3. These phage represent a second generation of phage clones selected against the four fluorophore dyes, Texas Red, Rhodamine Red, Oregon Green 514 and Fluorescein, respectively.

We isolated and sequenced a panel of independent phage clones from each of the TRS-3, RhRS-3, OGS-3 and FluS-3 phage sets to determine the sequences of the mutants (Table 2). In the Texas Red selection half of those sequenced encoded the parental amino acid structure. This indicated successful, though partial, selection against the parental binding characteristics under these conditions. Four of the sixteen TRS401 progeny cloned carried a conservative S12T substitution. Each of these substitutions occurred independently as it can be observed they are associated with additional, independent mutations. This suggests that the S12T substitution is probably an important change that enhances the affinity of the phage for the dye. Three progeny Texas Red fluorettes showed substitution at the second amino acid of histidine to P (found twice) or N. It is interesting to note that clone TRS311 carried both the H2P and the S12T mutations. Fewer mutant clones, only two, were observed for Rhodamine Red. The RhR401 phage clone might represent a local optima in affinity for Rhodamine Red. We found numerous in-frame deletions in the RhR401 fluorette-coded DNA sequences (about 33% of independent clones carrying large and small in-frame deletions in the fluorette moiety). This is an indicator of potential toxicity of the substituted mutant RhR401 fluorette sequences for bacteriophage growth and survival (data not shown). For Oregon Green 514 multiple different peptide sequences were selected, with only two independently containing the same, non-conservative, mutation (G2E). For Fluorescein the majority of peptide fluorettes selected were also not parental sequences. Several independent mutations were independently selected at fluorette positions 3 (N to S found twice), 5 (conservative change of F to Y found three times), 6 (conservative change E to D found twice), 9 (conservative E to D found twice), and 12 (conservative F to Y found 4 times). Also, certain

TABLE 2

Fluorophore dye-specific phage clones and peptide fluorette sequences. The second generation.

| Fluorophore dye carrier | Phage clone[a] | Phage clone frequency | Number of amino acid substitutions in the fluorette | Fluorette[b] |
|---|---|---|---|---|
| Texas Red | TR401 parent[c] | 8/16 | — | KHVQYWTQMFYS |
|  | TRS311 | 1/16 | 2 | .P.........T |
|  | TRS310 | 1/16 | 2 | .PA......... |
|  | TRS315 | 1/16 | 2 | .N.........T |
|  | TRS313 | 1/16 | 2 | .......H...T |
|  | TRS305 | 2/16 | 1 | ...........T |
|  |  |  |  | ...........T |
|  | TRS304 | 1/16 | 2 | N..H........ |
|  | TRS308 | 1/16 | 1 | T........... |
| Rhodamine Red | RhR401 parent[c] | 13/15 | — | IPHPPMYWTRVF |
|  | RhRS308 | 1/15 | 2 | ...R.....P.. |
|  | RhRS307 | 1/15 | 1 | L........... |
| Oregon Green 514 | OG403 parent[c] | 4/16 | — | HGWDYYWDWTAW |
|  | OGS316 | 1/16 | 2 | .E.E........ |
|  | OGS312 | 1/16 | 1 | .E.......... |
|  | OGS303 | 5/16 | 1 | ..........D. |
|  |  |  |  | ..........D. |
|  |  |  |  | ..........D. |
|  |  |  |  | ..........D. |
|  |  |  |  | ..........D. |
|  | OGS308 | 2/16 | 1 | ..........P. |
|  |  |  |  | ..........P. |
|  | OGS305 | 1/16 | 1 | ..........T. |

TABLE 2-continued

Fluorophore dye-specific phage clones and peptide fluorette sequences. The second generation.

| Fluorophore dye carrier | Phage clone[a] | Phage clone frequency | Number of amino acid substitutions in the fluorette | Fluorette[b] |
|---|---|---|---|---|
| | OGS302 | 1/16 | 1 | .....N...... |
| | OGS301 | 1/16 | 1 | Q........... |
| Fluorescein | OG402 parent[c] | 5/16 | — | YPNDFEWWEYYF |
| | FluS303 | 1/16 | 4 | ...E.D..D..Y |
| | FluS302 | 1/16 | 2 | ........D..Y |
| | FluS315 | 1/16 | 3 | .H..Y......Y |
| | FluS310 | 1/16 | 1 | ...........Y |
| | FluS307 | 1/16 | 2 | .....D.....L |
| | FluS311 | 1/16 | 3 | .TH.Y....... |
| | FluS312 | 1/16 | 1 | ....Y....... |
| | FluS313 | 1/16 | 1 | ..S......... |
| | FluS316 | 1/16 | 1 | ..S......... |
| | FluS304 | 1/16 | 1 | .-H......... |
| | FluS314 | 1/16 | 2 | ..Y........M | a) phage clones were isolated after three biopanning rounds with TR401-91CL, RhR401-91CL, OG403-91CL and OG402-91CL nonrandom combinatorial phage display peptide libraries (see text),
b) amino acid substitutions in mutant peptide fluorette vs the corresponding parent are shown, mutant peptide fluorette sequence is shown as many times as it was found (see phage clone frequency); dots designate the same amino acid as that in the corresponding parent; dash in a second position of the FluS304 fluorette designates in-frame deletion,
c) original parental clones and the parental clones carrying silent mutation(s) in peptide fluorette moiety.

positions appeared favored for change, i.e., 2, 3, and 12 with no strong bias for the substituted residue.

These mutations may be important for increasing the overall affinity of the peptide fluorette-fluorophore interaction. We tested one of each of the phage from the secondary screens for increases in avidity (Table 3). PEG-purified TR401 phage, TRS311 phage or the amplified Ph.D.-12 phage display peptide library phage as a negative control (input $1.5 \times 10^8$-$1.1 \times 10^{10}$ pfu with 2 to 5-fold increments) were incubated with 23.5 µl of BSA-blocked and washed Texas Red carrier beads in binding buffer (see above) in total volume 40 µl for 3 hr. Beads suspensions were centrifuged, the supernatants (unbound phage) were titrated and dissociation constants were measured via a standard linear Scatchard plot. For TR401 and TRS311 phage bound/unbound ratios were quite reliable (6.3-13.1 in the range of phage concentrations shown above). All binding experiments were performed in duplicate and titrations were performed in triplicate. This direct binding assay can reliably measure $K_d$ if it does not exceed ~1.5-2 nM. For higher $K_d$, bound/unbound ratios became unreliable (=1).

Other PEG-purified phage (input $5 \times 10^8$-$2.5 \times 10^{10}$ pfu with 2 to 5-fold increments) were bound to the respective fluorophore dye carriers essentially in the same manner as described above for Texas Red-specific phage. RhR401 and RhRS308, OG403 and OGS316, OG402 and FluS303 phage, were bound to the Rhodamine Red, Oregon Green 514 or Fluorescein carriers, respectively. Following binding the beads were quickly washed twice by 0.25 ml of TBS+ 0.1% Tween-20 and suspended in 10 ml TBS. 10 µl of suspension was mixed with ~$2 \times 10^8$ log-phase ER2537 cells and incubated 1 hr at 4° C. with slight shaking to allow phage adsorption. Several ten-fold dilutions of infected cells were mixed with noninfected ER2537 cells and plated in standard plaque assay (Sambrook et al., supra). All binding experiments and titrations were accomplished in duplicate. Nonspecific background of binding (determined with amplified Ph.D.-12 phage display peptide library phage) did not exceed more than 3% of specific binding in each case. For all above phage pfu/particle ratio was in the range 0.4-0.5.

The Texas Red progeny phage TRS311, which contained the apparently important S12T substitution, had a threefold increased avidity as compared to the TR401 parent. The affinity of the double mutant clone RhRS308 versus the parent was not even marginally improved (Table 3). For Oregon Green 514 the phage clone OGS316, which carried the G2E substitution, had a 2.7-fold higher avidity than its parent. The multiply substituted clone FluS303, which contained two putatively important changes, had a 6.5 fold increase in relative avidity. Thus, peptides can be matured to higher avidity. This likely is due to corresponding affinity increases for the individual peptide fluorette against its respective dye.

EXAMPLE 4

Binding of Peptides to Fluorophores in Solution

To identify peptide fluorettes that bind fluorophore dye independent of the full context of the pIII fusion bacteriophage protein we used synthetic peptides corresponding to the sequence of the selected fluorette region. We added to the peptide eight amino acids derived from the adjacent sequence of the pIII protein. This would accommodate any partial contributions of context from the pIII protein sequence. These were followed by a short GGG spacer and His$_6$ tag (see Table 4). We synthesized peptides from the original library screening that had been capable in solution of specifically binding each of the three dyes (Texas Red, Oregon Green 514, Fluorescein). The Texas Red peptides chosen were TR401 and its higher avidity progeny TRS311; a peptide corresponding to the unrelated Texas Red primary clone TR406 was also synthesized. The Oregon Green 514 clones OG401 and OG403 were synthesized to test, in part, the observation that both contained a common motif YWDW which might represent a common binding motif for Oregon Green 514. Note that the OG401 clone also bound to Fluorescein in the original screening. The other clone which bound to both Oregon Green and Fluorescein in the primary screen, OG402, was synthesized. The peptide derived from a secondary screen against Fluorescein, FluS303, which demonstrated a 6.5-fold higher affinity was also synthesized. No peptides for Rhodamine Red were synthesized.

Peptides were bound to cobalt ion-coated Sepharose beads and the resultant peptide-coated beads were incubated with corresponding fluorophore dyes, washed, and visualized for dye binding. The same amounts of Texas Red-specific peptides PepTR401, PepTRS311, PepTR406 as well as nonspecific peptide PepControl (see Table 4) were bound via $His_6$ tag to the TALON Metal Affinity Resin (Clontech) in TBS buffer essentially as described by manufacturer's protocol. Beads (5 μl) were washed twice with 0.5 ml TBS to remove unbound peptide and incubated with 0.5 μM Texas Red in 40 μl of TBS buffer for 1 hr at RT. Finally, the beads were washed three times with 0.3 ml TBS to remove unbound dye. Fluorescent and nonfluorescent control beads were photographed with 10-fold magnification on fluorescent microscope Axiophot (Zeiss) using Rhodamine Red/Texas Red filter with 5" exposure.

Most peptides failed to bind dyes to any detectable degree. However, Texas Red peptides PepTR401 and PepTRS311 showed significant binding to Texas Red while they bound to neither Oregon Green 514 nor Fluorescein (data not shown). PepTR406 did not bind to Texas Red, however. Lack of dye binding might be due to low peptide affinity for cognate dyes and/or because the binding requires contributions from the pIII fusion protein not present in these peptides.

The above test only checks for bound dye that remains fluorescent at the wavelengths tested. Binding of fluorophore dyes to specific peptides might result in changes in the fluorescence spectra of bound dye versus the spectra of free dye. Or, one might observe an increase or quenching of fluorescence. We mixed concentrated peptide with 50 nM of the corresponding dye in solution and determined the excitation and emission spectra of the resulting mixture. No detectable changes in peak excitation nor emission were observed for peptides selected against Oregon Green 514 or Fluorescein (data not shown), nor for PepTR406, nor for a control peptide (FIG. 5B).

Figure 5A:
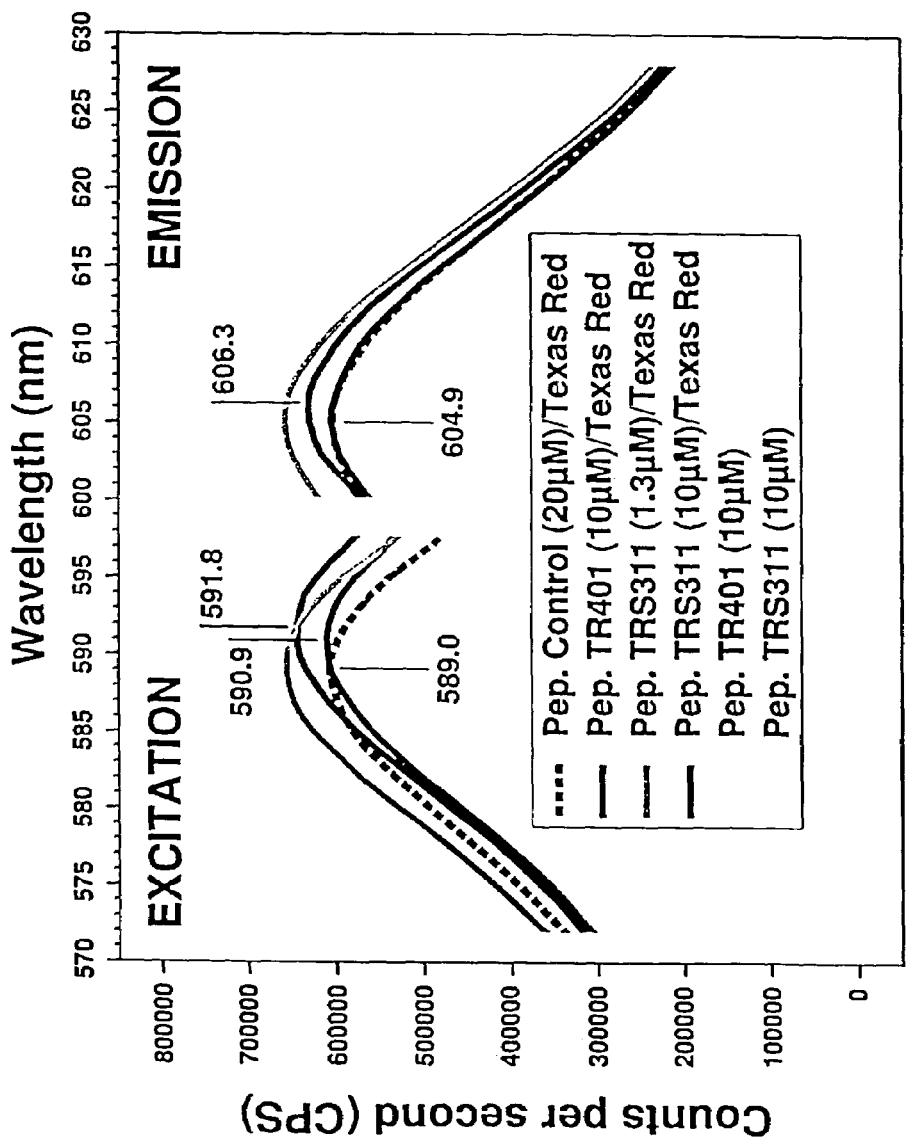
FIGS. 5A and 5B. Peptide—Texas Red binding. Excitation and emission spectra. Peptides at the noted concentrations were incubated with Texas Red (50 nM), or without, in 0.6 ml of TBS for 1 hr at room temperature (RT). Samples were scanned on a spectrofluorimeter (SPEX Fluoromax (Jobin Yvon-SPEX Instruments Co.)). Peak excitation or emission positions are shown in the figure using vertical bars. Excitation and excitation/emission peak shifts for PepTR401 (10 μM)/Texas Red and PepTRS311 (10 μM)/Texas Red complexes, respectively (A), were reproducible in three independent experiments. The results of a single experiment are presented.
Figure 5B:
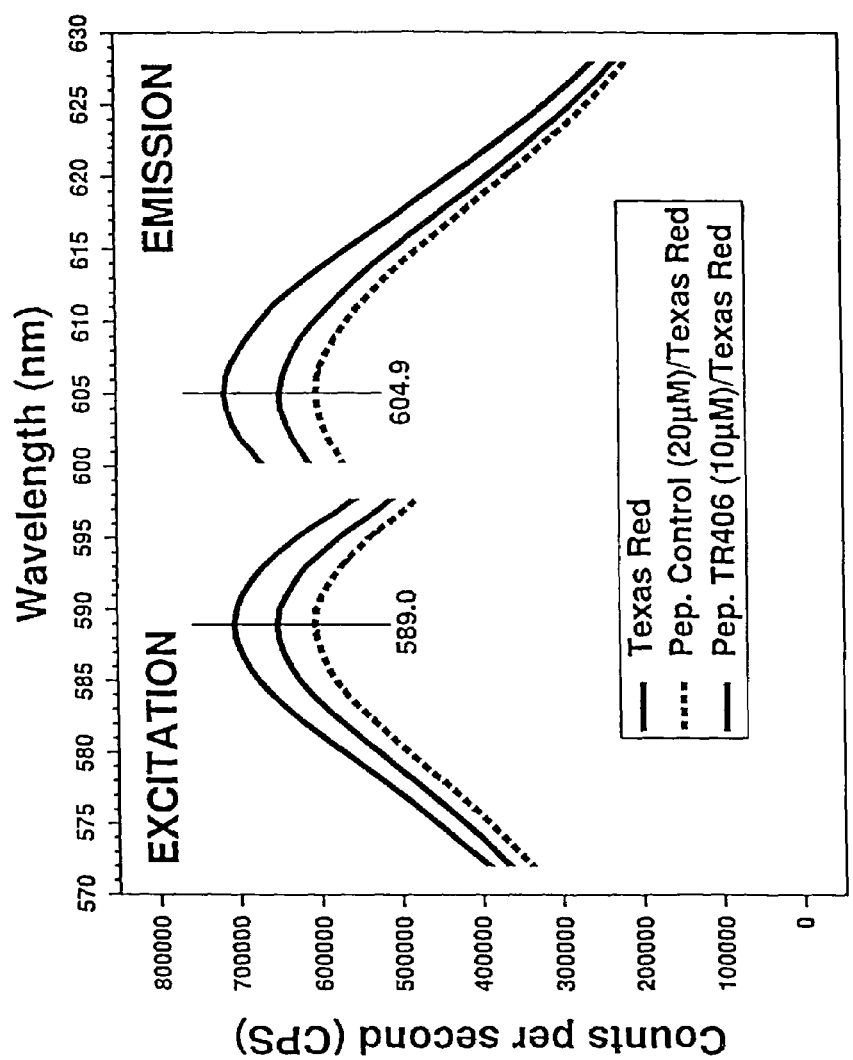

However, the peak positions of the excitation and emission spectra of soluble Texas Red bound to 10 μM PepTR401 was shifted relative to Texas Red alone or as compared to a mixture of Texas Red and a nonspecific control peptide (FIG. 5A). A+1.9 nm peak excitation shift with PepTR401 was observed. The peptide was checked against Fluorescein as a nonspecific control and showed no shift in the Fluorescein excitation or emission spectra. An approximate peak excitation shift of +2.8 nm was effected upon dye binding with PepTRS311. Interestingly, although PepTR401 had a shift in its peak excitation, no emission shift change was elicited upon binding fluorophore. However, PepTRS311 did manifest a significant +1.4 nM peak emission shift in its spectra. We checked all other excitation and emission wavelengths and the changes observed correspond to a largely global shift in the spectra. No other significant changes in local optima were observed (data not shown).

Interestingly, the TR401 peptide is the progenitor of the TRS311 peptide. Thus, the two substitutions H2P and S12T result not only in an increased binding, but also in an apparent differences in the excitation spectra elicited. Moreover, though both show a shift in the excitation only the selected, higher affinity, PepTRS311 had a peak emission spectra shift. Thus, one or both of the two substitutions, H2P or S12T, are critical for shifting the spectra of the emission profile.

We attempted with these findings to obtain an affinity measurement for the higher affinity TRS311 peptide. Peptides in different concentrations (1.3-20 μM) were incubated with Texas Red (50 nM) in 0.6 ml of TBS buffer for 1 hr at RT. Excitation and emission spectra of samples were obtained by using spectrofluorimeter SPEX Fluoromax (Jobin Yvon-SPEX Instruments Co.) and DataMax software package. Peak positions were automatically calculated by software. List mode data was saved for other analyses.

Reduction of the concentration of PepTRS311 from 10 μM to 1.3 μM reduced slightly, but not completely, the change in peak excitation position (FIG. 5A). The narrow dynamic range of the shift and the broad emission spectra provided for a limited ability to obtain an approximate measure of the affinity. Affinity measurements calculated roughly from these results place the affinity of the peptide for the fluorophore at 0.1-0.5 μM. Further examination of this issue by other approaches is required to obtain more accurate reflections of the affinity and off-rates. However, together with the agarose bead-binding data we can conclude that we have successfully selected for peptides with sufficient affinity to bind small molecule fluorophore dyes in solution. In addition, the binding is specific and the spectral qualities of the dyes can be modulated dependent upon modifications of the bound peptide.

TABLE 3

Phage - fluorophore dye binding affinity. Dissociation constants.

| Fluorophore dye carrier | Phage Clone | Fluorette[a] | $K_d$ (nM) | Affinity increase (fold)[b] |
|---|---|---|---|---|
| Texas Red | TR401 parent | KHVQYWTQMFYS | 0.27 | 3.0 |
| | TRS311 | .P.........T | 0.09 | |
| Rhodamine Red | RhR401 parent | IPHPPMYWTRVF | 23.0 | no increase |
| | RhRS308 | ...R.....P.. | 21.5 | |
| Oregon Green 514 | OG403 parent | HGWDYYWDWTAW | 6.4 | 2.7 |
| | OGS316 | .E.E........ | 2.4 | |
| Fluorescein | OG402 parent | YPNDFEWWEYYF | 17.4 | 6.5 |
| | FluS303 | ...E.D..D..Y | 2.7 | |

[a] amino acid substitutions in mutant peptide fluorette vs the corresponding parent are shown; dots designate the same amino acid as that in the corresponding parent;
[b] mutant peptide fluorette vs the corresponding parental peptide fluorette.

TABLE 4

Fluorette-carrying peptides.

| Fluorophore dye | Peptide[a] | Sequence[b] |
|---|---|---|
| Texas Red | Pep. TR401 | K<u>HVQYWTOMFYS</u>GGGSAETVGGGHHHHHH |
| | Pep. TRS311 | K<u>PVQYWTOMFYT</u>GGGSAETVGGGHHHHHH |
| | Pep. TR406 | D<u>FLQWKLARQKP</u>GGGSAETVGGGHHHHHH |
| Oregon Green 514 | Pep. OG403 | H<u>GWDYYWDWTAW</u>GGGSAETVGGGHHHHHH |
| | Pep. OG401[c] | A<u>SDYWDWEWYYS</u>GGGSAETVGGGHHHHHH |
| | Pep. OG402[c] | Y<u>PNDFEWWEYYF</u>GGGSAETVGGGHHHHHH |
| Fluorescein | Pep. FluS303 | Y<u>PNEFDWWDYYY</u>GGGSAETVGGGHHHHHH |
| | Pep. Control[d] | A<u>SGSGASGSAGS</u>GGGSAETVGGGHHHHHH |

[a]peptide names reflect the names of phage clones carrying respective fluorettes except Pep. Control (see Tables 1 and 2)
[b]first twenty amino acids of the peptides are the same as in the pIII fusion protein of the corresponding phage clones except Pep. Control (see Tables 1 and 2 and also New England Biolabs "Ph.D.-12 Phage Display Peptide Library Kit" manual), thus, amino acids 1-12 are the fluorette potion (double underlined) and amino acids 13-20 are the distal pIII fusion part (underlined). Amino acids 21-29 contain a small GGG spacer followed by $His_6$ tag (shown in regular case). (SEQ ID NOS:41-48)
[c]specific for both Oregon Green 514 and Fluorescein (see Table 1).
[d]nonspecific control peptide synthesized for specificity check.

EXAMPLE 5

Constrained Texas Red-Binding Peptides

Constrained Texas Red-binding peptides were identified via five rounds of biopanning of a mixture of two constrained phage display libraries against a polymer carrier with covalently bound Texas Red. Two libraries contained SKVILFE-flanked nine or thirteen amino acid variable region in the N-terminal part of M13 bacteriophage pIII protein. The structure of the libraries were as follows:

The flexible linker or spacer GPAG is encoded by a nucleotide sequence containing FseI restriction endonuclease site. The flexible linker or spacer GAPG is encoded by a nucleotide sequence containing AscI restriction endonuclease site. Both FseI and AscI restriction enzymes are rare eight-cutters. Thus, upon a double enzyme digestion, a universal cassette-library or cassettes containing specific sequences can be conveniently exchanged between different vector/host systems or different dimerizers of a choice (e.g., pair of cysteines, coiled coil structures, etc.).

<u>GGGSKVILFEGPAG</u> (X)$_{9\ or\ 13}$ <u>GAPGSKVILFEGGPG</u> (SEQ ID NO:93)- (pIII protein)

SKVILFE-dimerizers are underlined. Flexible linkers or spacers GGG, GPAG (SEQ. ID NO:94), GAPG (SEQ.ID NO:95) and GGPG (SEQ. ID NO:96) are double underlined. X represents any amino acid.

Biopanning against carrier with Texas Red ultimately revealed at least seven different Texas Red-binding constrained peptides (both 9- and 13-mers in a variable part):

```
GGGSKVILFEGPAG RTIWEPKEASNHT GAPGSKVILFEGGPG  (TRP501)  SEQ.ID NO:97
GGGSKVILFEGPAG WSKMGHTVT     GAPGSKVILFEGGPG  (TRP505)  SEQ.ID NO:98
GGGSKVILFEGPAG RWTWEPISE     GAPGSKVILFEGGPG  (TRP512)  SEQ.ID NO:99
GGGSKVILFEGPAG GNQKCLQHNRCST GAPGSKVILFEGGPG  (TRP518)  SEQ.ID NO:100
GGGSKVILFEGPAG SQTWSFPEH     GAPGSKVILFEGGPG  (TRP526)  SEQ.ID NO:101
GGGSKVILFEGPAG EPMARPWERKQDR GAPGSKVILFEGGPG  (TRP527)  SEQ.ID NO:102
GGGSKVILFEGPAG GTLSATRPYGRQW GAPGSKVILFEGGPG  (TRP541)  SEQ.ID NO:103
```

Consensus motifs can be observed within these peptides (e.g., RXXWEP (SEQ ID NO:104), WEP and TW; see Table 5) that suggests structural features common to the peptides that allow for efficient binding. Interestingly, no said constrained peptide has a significant homology with linear Texas Red-binding peptides.

Binding affinity of phage clones revealed the most avid binders, TRP512 phage and TRP501 phage, with $K_d$ equal to 25 pM and 80 pM, respectively. Other five phage clones were much less avid with $K_d \leq 5$ nM (see Table 5).

Figure 6:
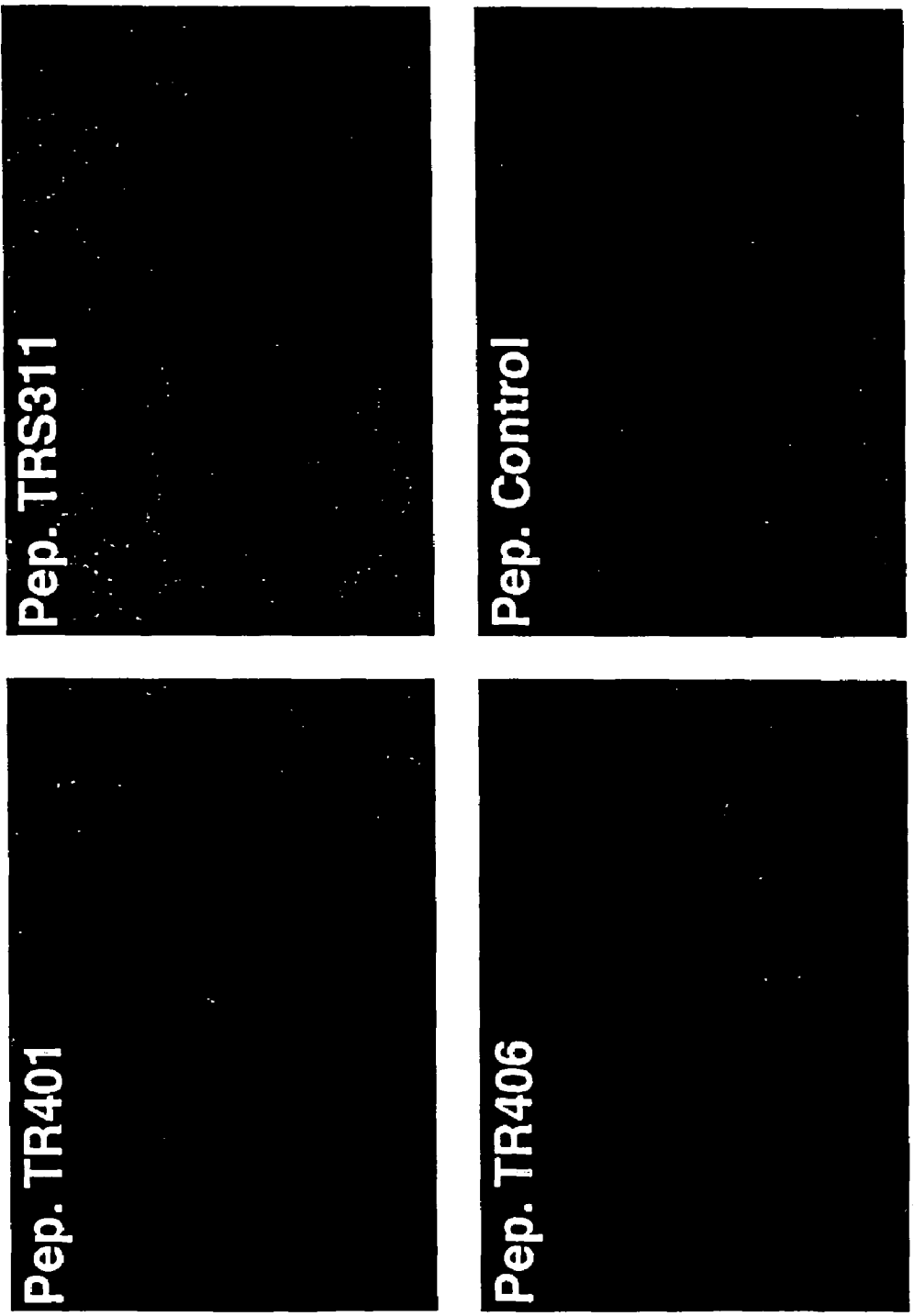
FIG. 6. Texas Red-specific peptide PepTR401 (Panel A), PepTRS311 (Panel B), PepTR406 (Panel C) and nonspecific PepControl (Panel D) (see peptide sequences in Table 4) were bound via $His_6$ tag to cobalt ion-containing Sepharose beads. The peptide coated beats were washed and incubated with 0.5 micromolar Texas Red in TBS for 1 hour at room temperature followed by several washings of beads in order to remove unbound dye. Fluorescent and nonflourescent control beads were photographed on fluorescent microscope Axiophot (Zeiss) using Rhodamine Red/Texas Red filter with the same time exposure for every sample. All binding experiments were accomplished in three parallels and results of a single experiments are shown.
Figure 7:
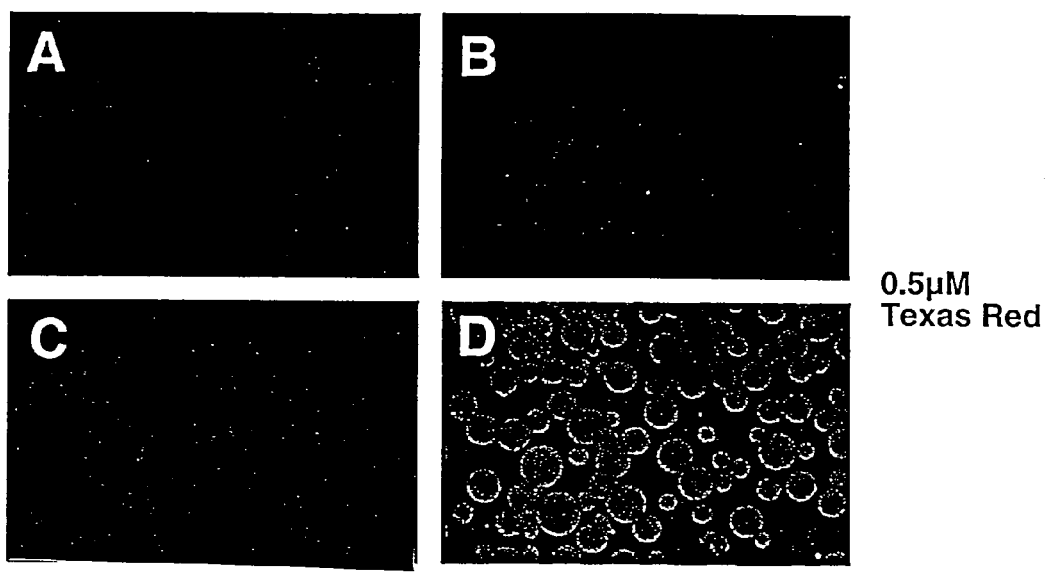
FIGS. 7A-D. Peptide—Texas Red binding. Texas Red-specific peptides TR401 (linear) (FIG. 6B), TRP501 (SKVILFE-flanked) (FIG. 6C), TRP512 (SKVILFE-flanked) (FIG. 6D), and nonspecific peptide (SKVILFE-flanked) (FIG. 6A) as a negative control were bound via polyhistidine ($His_6$) tag to cobalt ion-containing Sepharose beads. The peptide-coated beads were washed and incubated with 0.5 μM Texas Red in TBS buffer for 1 hour at room temperature followed by several washings of beads in order to remove unbound dye. Fluorescent and nonfluorescent control beads were photographed on fluorescent microscope Axiophot (Zeiss) using Rhodamine Red/Texas Red filter with the same time exposure for every sample. All binding experiments were accomplished in duplicate and results of a single experiment are shown.

Binding of synthetic peptides (nonspecific peptide, TR401, TRP501 and TRP512) to Texas Red is shown in FIGS. 6B-C.

Binding affinity of synthetic TRP501 peptide is measured as $K_d \approx 200$ nM ($\approx$8-fold more avid than linear TR401 and TRS311 peptides). Binding affinity of synthetic TRP512 peptide is measured as $K_d \approx 10$ nM ($\approx$160-fold more avid than linear TR401 and TRS311 peptides).

CONCLUDING REMARKS

The foregoing description details specific methods which can be employed to practice the present invention. Having detailed such specific methods, those skilled in the art will well enough know how to devise alternative reliable methods at arriving at the same information in using the fruits of the present invention. Thus, however detailed the foregoing may appear in text, it should not be construed as limiting the overall scope thereof; rather, the ambit of the present invention is to be determined only by the lawful construction of the appended claims. All documents cited herein are hereby expressly incorporated by reference.

TABLE 5

Texas Red - specific phage clones carrying SKVILFE - flanked fluorettes.

| Phage clone[a] | Phage clone frequency | Fluorette size (a.a.) | Fluorette | Fluorette consensus | Fluorette net charge[b] | Fluorette hydrophobicity[c] | Phage clone $K_d$ |
|---|---|---|---|---|---|---|---|
| TRP501* | 42/48 | 13 | RTIWEPKEASNHT | RXXWEP | 0 (−2/+2) | 3/13 | 80 pM |
| TRP505 | 1/48 | 9 | WSKMGHTVT | WEP | +1 | 2/9 | >5 nM |
| TRP512 | 1/48 | 9 | RWTWEPISE | TW | −1 (−2/+1) | 3/9 | 25 pM |
| TRP518 | 1/48 | 13 | GNQKCLQHNRCST | | +2 | 1/13 | >5 nM |
| TRP526 | 1/48 | 9 | SQTWSFPEH | | −1 | 2/9 | >5 nM |
| TRP527 | 1/48 | 13 | EPMARPWERKQDR | | +1 (−3/+4) | 2/13 | >5 nM |
| TRP541 | 1/48 | 13 | GTLSATRPYGRQW | | +2 | 4/13 | >5 nM |

[a]phage clones were isolated after five biopanning rounds with a mixture of combinatorial P71R4-CL-9 & P71R4-Cl-13 phage display peptide libraries
[b]−1 (D, E) or +1 (K, R)
[c]number of hydrophobic amino acids (A, V, L, I, W, Y, F) per total number of fluorette amino acids
*phage clone is represented in the corresponding group at least twice

We claim:

1. A peptide comprising an amino acid sequence, $X_1$-$X_2$-$X_3$-$X_4$-Y-W-T-$X_5$-M-F-Y-$X_6$ (SEQ ID NO:116), wherein,
   $X_1$ is selected from the group consisting of K, N and T;
   $X_2$ is selected from the group consisting of H, P, and N;
   $X_3$ is selected from the group consisting of A and V;
   $X_4$ is selected from the group consisting of H and Q;
   $X_5$ is selected from the group consisting of H and Q;
   $X_6$ is selected from the group consisting of S and T.

2. The peptide of claim 1, wherein the peptide comprises the amino acid sequence of KPVQYWTQMFYT (SEQ ID NO:15).

3. The peptide of claim 1, wherein the peptide comprises the amino acid sequence of KHVQYWTQMFYS (SEQ ID NO:1).

4. The peptide of claim 1, wherein the peptide comprises the amino acid sequence of KPAQYWTQMFYS (SEQ ID NO:16).

5. The peptide of claim 1, wherein the peptide comprises the amino acid sequence of KNVQYWTQMFYT (SEQ ID NO:17).

6. The peptide of claim 1, wherein the peptide comprises the amino acid sequence of KHVQYWTHMFYT (SEQ ID NO:18).

7. The peptide of claim 1, wherein the peptide comprises the amino acid sequence of KHVQYWTQMFYT (SEQ ID NO:19).

8. The peptide of claim 1, wherein the peptide comprises the amino acid sequence of NHVHYWTQMFYS (SEQ ID NO:20).

9. The peptide of claim 1, wherein the peptide comprises the amino acid sequence of THVQYWTQMFYS (SEQ ID NO:21).

10. The peptide of claim 1, wherein the amino acid sequence comprises naturally-occurring amino acids.

11. The peptide of claim 1, wherein the peptide is fused to a presentation structure.

12. A complex comprising a fluorophore dye and a peptide according to claim 1, wherein said peptide specifically binds to the Texas Red fluorophore dye.

13. A method of binding a peptide to Texas Red fluorophore dye comprising;
   contacting said Texas Red fluorophore dye with the peptide according to claim 1;
   wherein said contacting provides for binding of the peptide to the Texas Red fluorophore dye.

14. A method of detecting a fluorette comprising:
   contacting a fluorette with Texas Red fluorophore dye to form a fluorette-dye complex, wherein the fluorette comprises a peptide according to claim 1;
   detecting the presence of the dye complex.

15. The method of claim 13, wherein the fluorette is linked to a target analyte.

* * *

UNITED STATES PATENT AND TRADEMARK OFFICE
CERTIFICATE OF CORRECTION

| | | |
|---|---|---|
| PATENT NO. | : 7,332,356 B2 | Page 1 of 1 |
| APPLICATION NO. | : 10/692151 | |
| DATED | : February 19, 2008 | |
| INVENTOR(S) | : Garry P. Nolan | |

It is certified that error appears in the above-identified patent and that said Letters Patent is hereby corrected as shown below:

Column 9:

- Claim 12 line 21: Delete "a" and replace it with --Texas Red--.

Signed and Sealed this

Twenty-fourth Day of June, 2008

JON W. DUDAS
*Director of the United States Patent and Trademark Office*